(12) United States Patent
Masciadri et al.

(10) Patent No.: US 6,743,789 B2
(45) Date of Patent: Jun. 1, 2004

(54) SUBSTITUTED IMIDAZO[1,5-A][1,2,4]TRIAZOLO[4,3-D][1,4]BENZODIAZEPINE DERIVATIVES

(75) Inventors: Raffaello Masciadri, Basle (CH); Andrew William Thomas, Birsfelden (CH); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 79 days.

(21) Appl. No.: 10/007,883

(22) Filed: Nov. 8, 2001

(65) Prior Publication Data

US 2002/0103371 A1 Aug. 1, 2002

(30) Foreign Application Priority Data

Nov. 16, 2000 (EP) .............................. 00124332

(51) Int. Cl.$^7$ ..................... A61K 31/55; A61P 25/28; C07D 487/22
(52) U.S. Cl. ..................... 514/219; 540/555
(58) Field of Search ........................ 514/219; 540/555

(56) References Cited

U.S. PATENT DOCUMENTS

| 4,772,599 A | 9/1988 | Watjen ................. 514/220 |
| 5,387,585 A | 2/1995 | Borer et al. ............ 514/219 |

FOREIGN PATENT DOCUMENTS

EP 0 519 307 12/1992

OTHER PUBLICATIONS

Max Gerecke et al., *Heterocycles*, vol. 39, No. 2, pp. 693–721 (1994).
McNamara & Skelton, *Psychobiology*, vol. 21(2), pp. 101–108 (1993).

Primary Examiner—Brenda Coleman
(74) Attorney, Agent, or Firm—George W. Johnston; Patricia S. Rocha-Tramaloni; Kimberly J. Prior

(57) ABSTRACT

The present invention is a compound of formula

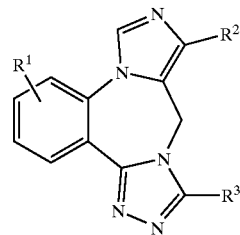

The compound and derivatives or pharmaceutically acceptable salts thereof of the invention have a good affinity and selectivity to the GABA A α5 receptor and are useful for the treatment of diseases related to this receptor.

18 Claims, No Drawings

SUBSTITUTED IMIDAZO[1,5-A][1,2,4]TRIAZOLO[4,3-D][1,4]BENZODIAZEPINE DERIVATIVES

BACKGROUND

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in Psychobiology, 21:101–108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY

The present invention is concerned with substituted imidazo[1,5-a][1,2,4]triazolo[4,3-d][1,4]benzodiazepine derivatives of the following formula

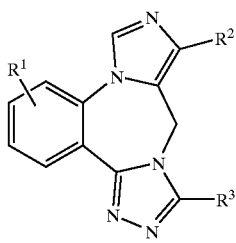

I wherein
$R^1$ is hydrogen, halogen, lower alkyl, lower alkoxy, hydroxy, cyano, trifluoromethyl, trifluoromethoxy or lower alkylthio;

$R^2$ is —C(O)O-lower alkyl, unsubstituted isoxazol, 1,2,4-oxadiazol-3-yl or 1,2,4-oxadiazol-5-yl, or isoxazol, 1,2,4-oxadiazol-3-yl or 1,2,4-oxadiazol-5-yl, substituted by lower alkyl, trifluoromethyl or cycloalkyl;

$R^3$ is hydrogen, lower alkyl, —$(CH_2)_n$-cycloalkyl, —$(CH_2)_n$-halogen, —$(CH_2)_n$-pyridin-4-yl, or unsubstituted —$(CH_2)_n$-phenyl, or —$(CH_2)_n$-phenyl substituted by one or two substituents selected from the group consisting of lower alkoxy, halogen, —$SO_2CH_3$, phenyl, $OCF_3$, nitro, $CF_3$, —$NR2$, or is unsubstituted —$(CH_2)_n$-indolyl, -or —$(CH_2)_n$-indolyl substituted by lower alkyl or lower alkoxy, or is pyrrolidinyl-5-oxo, —C(O)—$NR_2$, —$(CH_2)_n$—OH, —$(CH_2)_n$—$NR_2$ or —$(CH_2)_n$-benzo[1,3]dioxole;

R is hydrogen or lower alkyl; and
n is 0, 1, 2 or 3;

or a pharmaceutically acceptable acid addition salt thereof with the exception of the following compounds:

A.) Ethyl 9H-imidazo[1,5-a][1,2,4]triazolo[3,4-d][1,4]benzodiazepine-10-carboxylate, B.) 10-(3-cyclopropyl-1,2,4-oxadiazol-5-yl)-9H-imidazo[1,5-a][1,2,4]triazolo[4,3-d][1,4]benzodiazepine, C.) ethyl 3-fluoro-9H-imidazo[1,5-a][1,2,4]triazolo[4,3-d][1,4]benzodiazepine-10-carboxylate, D.) 10-(3-cyclopropyl-1,2,4-oxadiazol-5-yl)-3-fluoro-9H-imidazo[1,5-a][1,2,4]triazolo[4,3-d][1,4]benzodiazepine, E.) ethyl 3-chloro-9H-imidazo[1,5-a][1,2,4]triazolo[4,3-d][1,4]benzodiazepine-10-carboxylate or F.) 3-chloro-10-(3-cyclopropyl-1,2,4-oxadiazol-5-yl)-9H-imidazo[1,5-a][1,2,4]triazolo[4,3-d][1,4]benzodiazepine.

The above mentioned specific (A–F) imidazo[1,5-a][1,2,4]triazolo-[4,3-d][1,4]benzodiazepine derivatives have already been described (Heterocycles, Vol. 39, No. 2, 1994), however, in this document it is mentioned that these compounds unexpectedly show low affinities for BzR (benzodiazepine receptor) and therefore are devoid of anxiolytic activity. Surprisingly, it has now been found that this class of compounds show high affinity and selectivity for GABA A α5 receptor binding sites indicative of utility as cognitive enhancer or for the treatment of cognitive disorders like Alzheimer's disease.

Objects of the present invention are compounds of formula I and pharmaceutically acceptable salts, the preparation of the above mentioned compounds, medicaments containing them and their manufacture as well as the use of the above mentioned compounds in the control or prevention of illnesses, especially of illnesses and disorders of the kind referred to earlier or in the manufacture of corresponding medicaments.

The most preferred indication in accordance with the present invention is Alzheimer's disease.

DETAILED DESCRIPTION

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "cycloalkyl" denotes a cyclic alkyl ring residue, having from 3 to 7 carbon ring atoms, for example, cyclopropyl, cyclopentyl or cyclohexyl.

The term "lower alkylthio" means the group —S—$C_{1-7}$-alkyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Exemplary preferred are compounds, which have a binding activity (Ki) of lower than 15 nM; are selective for GABA A α5 subunits; and are relatively free of activity at GABA A α1, α2 and α3 receptor binding sites.

Preferred compounds of formula I for use in the above mentioned disease are those, in which $R^2$ is the group —C(O)O-lower alkyl.

Exemplary preferred are compounds of this group, wherein $R^3$ is hydrogen and $R^1$ is hydrogen, methoxy, methyl, —$SCH_3$ or halogen, for example the following compounds:

Ethyl 3-methoxy-9H-imidazo[1,5-a][1,2,4]triazolo[4,3-d][1,4]-benzodiazepine-10-carboxylate,
ethyl 3-methyl-9H-imidazo[1,5-a][1,2,4]triazolo[3,4-d][1,4]benzodiazepine-10-carboxylate,
ethyl 3-bromo-9H-imidazo[1,5-a][1,2,4]triazolo[4,3-d][1,4]-benzodiazepine-10-carboxylate,
ethyl 9H-imidazo[1,5-a][1,2,4]triazolo[3,4-d][1,4]benzodiazepine-10-carboxylate,
ethyl 3-fluoro-9H-imidazo[1,5-a][1,2,4]triazolo[4,3-d][1,4]benzodiazepine-10-carboxylate or
ethyl 3-chloro-9H-imidazo[1,5-a][1,2,4]triazolo[4,3-d][1,4]benzodiazepine-10-carboxylate.

Further preferred compounds of this group are those, wherein $R^3$ is —$CH_2OH$, —$(CH_2)_2$-methylenedioxyphenyl, methyl, —$CH_2$-indolyl, optionally substituted by methoxy, or is $CH_2$-phenyl, substituted by —$SO_2CH_3$, phenyl, —$OCF_3$, —$N(CH_3)_2$, $NO_2$ or methoxy, and $R^1$ is methoxy, chloro or bromo, for example the following compounds:

Ethyl 3-methoxy-7-methyl-9H-imidazo[1,5-a][1,2,4]triazolo[4,3-d][1,4]-benzodiazepine-10-carboxylate,
ethyl 3-methoxy-7-(1H-indol-3-ylmethyl)-9H-imidazo[1,5-a][1,2,4]triazolo[4,3-d][1,4]-benzodiazepine-10-carboxylate,
ethyl 7-hydroxymethyl-3-methoxy-9H-imidazo[1,5-a][1,2,4]triazolo[4,3-d][1,4]-benzodiazepine-10-carboxylate,
ethyl 3-methoxy-7-(3-methoxybenzyl)-9H-imidazo[ 1,5-a][1,2,4]triazolo[4,3-d][1,4]-benzodiazepine-10-carboxylate,
ethyl 3-methoxy-7-[(7-methoxy-1H-indol-3-yl)methyl]-9H-imidazo[1,5-a][1,2,4]triazolo[4,3-d][1,4]-benzodiazepine-10-carboxylate,
ethyl-3-bromo-7-(1H-indol-3-ylmethyl)-9H-imidazo[1,5-a][1,2,4]triazolo[4,3-d][1,4]-benzodiazepine-10-carboxylate,
ethyl-3-bromo-7-(3-methoxy-benzyl)-9H-imidazo[1,5-a][1,2,4]triazolo[4,3-d][1,4]-benzodiazepine-10-carboxylate,
ethyl 7-[2-benzo[1,3]dioxol-5-yl)-ethyl]-3-chloro-9H-imidazo[1,5-a][1,2,4]triazolo[4,3-d][1,4]-benzodiazepine-10-carboxylate,
ethyl 7-(4-methanesulfonyl-benzyl)-3-methoxy-9H-imidazo[1,5-a][1,2,4]triazolo[4,3-d][1,4]-benzodiazepine-10-carboxylate,
ethyl 3-methoxy-7-[(biphenyl-4-yl)methyl]-9H-imidazo[1,5-a][1,2,4]triazolo[4,3-d][1,4]-benzodiazepine-10-carboxylate,
ethyl 3-methoxy-7-(4-trifluoromethoxy-benzyl)-9H-imidazo[1,5-a][1,2,4]triazolo[4,3-d][1,4]-benzodiazepine-10-carboxylate,
ethyl 3-chloro-7-(4-nitro-benzyl)-9H-imidazo[1,5-a][1,2,4]triazolo[4,3-d][1,4]-benzodiazepine-10-carboxylate,
ethyl 7-(4-dimethylamino-benzyl)-3-methoxy-9H-imidazo[1,5-a][1,2,4]triazolo[4,3-d][1,4]-benzodiazepine-10-carboxylate or
ethyl 3-bromo-7-(4-dimethylamino-benzyl)-9H-imidazo[1,5-a][1,2,4]triazolo[4,3-d][1,4]-benzodiazepine-10-carboxylate.

Further preferred compounds for use in the above mentioned disease are those, in which $R^2$ is the group 3-cyclopropyl-[1,2,4]oxadiazol-5-yl.

Exemplary preferred are compounds of this group, wherein $R^3$ is hydrogen and $R^1$ is hydrogen, methoxy, methyl, —$SCH_3$ or halogen, for example the following compounds:

10-(3-Cyclopropyl-1,2,4-oxadiazol-5-yl)-3-methoxy-9H-imidazo[1,5-a][1,2,4]triazolo[4,3-d][1,4]benzodiazepine,
10-(3-cyclopropyl-1,2,4-oxadiazol-5-yl)-3-methyl-9H-imidazo[1,5-a][1,2,4]triazolo[4,3-d][1,4]benzodiazepine,
10-(3-cyclopropyl-1,2,4-oxadiazol-5-yl)-3-bromo-9H-imidazo[1,5-a][1,2,4]triazolo[4,3-d][1,4]benzodiazepine,
10-(3-cyclopropyl-1,2,4-oxadiazol-5-yl)-3-methylsulfanyl-9H-imidazo[1,5-a][1,2,4]triazolo[4,3-d][1,4]benzodiazepine,
10-(3-cyclopropyl-1,2,4-oxadiazol-5-yl)-9H-imidazo[1,5-a][1,2,4]triazolo[4,3-d][1,4]benzodiazepine,
10-(3-cyclopropyl-1,2,4-oxadiazol-5-yl)-3-fluoro-9H-imidazo[1,5-a][1,2,4]triazolo[4,3-d][1,4]benzodiazepine,
3-chloro-10-(3-cyclopropyl-1,2,4-oxadiazol-5-yl)-9H-imidazo[1,5-a][1,2,4]triazolo[4,3-d][1,4]benzodiazepine or
3-chloro-10-(5-cyclopropyl-1,2,4-oxadiazol-3-yl)-9H-imidazo[1,5-a][1,2,4]triazolo[4,3-d][1,4]benzodiazepine.

Further preferred are compounds from this group, wherein $R^3$ is —$CH_2$-indolyl or —$CH_2$-phenyl, optionally substituted by —$N(CH_3)_2$ and $R^1$ is chloro or bromo, for example the following compounds:

10-(3-cyclopropyl-1,2,4-oxadiazol-5-yl)-7-(4-dimethylamino-benzyl)-3-bromo-9H-imidazo[1,5-a][1,2,4]triazolo[4,3-d][1,4]benzodiazepine,
3-Chloro-10-(5-cyclopropyl-1,2,4-oxadiazol-3-yl)-7-(1H-indol-3-ylmethyl)-9H-imidazo[1,5-a][1,2,4]triazolo[4,3-d][1,4]benzodiazepine or
7-Benzyl-3-chloro-10-(5-cyclopropyl-1,2,4-oxadiazol-3-yl)-9H-imidazo[1,5-a][1,2,4]triazolo[4,3-d][1,4]benzodiazepine.

The present compounds of formula I and their pharmaceutically acceptable salts may be prepared by methods known in the art, for example, by processes described below, which process comprises reacting a compound of formula

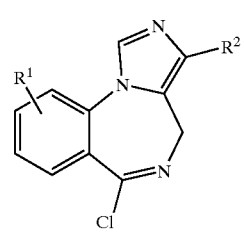

II with a compound of formula

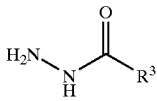

to give a compound of formula

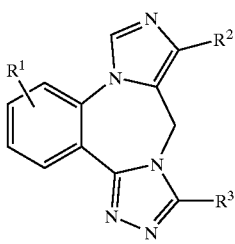

wherein the substituents R¹–R³ have the significances given above, or reacting a compound of formula

IV

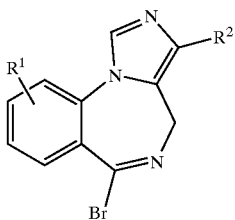

with

to give a compound of formula

V

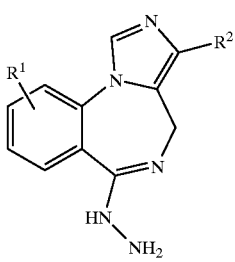

and cyclizing this compound with

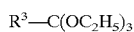

VI to a compound of formula

III

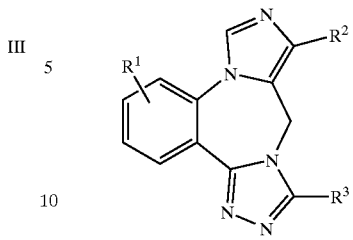

wherein R¹–R³ have the significances given above, or modifying one or more substituents R¹–R³ within the definitions given above, and if desired, converting the compounds obtained into a pharmaceutically acceptable acid addition salt.

The compounds of formula I in accordance with reaction variant a) may be prepared as follows: A compound of formula II, for example 6-chloro-8-methoxy-4H-2,5,10b-triaza-benzo[e]azulene-3-carboxylic acid ethyl ester or 6-chloro-8-methyl-4H-2,5,10b-triaza-benzo[e]azulene-3-carboxylic acid ethyl ester or 6-chloro-8-bromo-4H-2,5,10b-triaza-benzo[e]azulene-3-carboxylic acid ethyl ester is treated with a compound of formula III, for example with formylhydrazine, acethydrazine, indole-3-acetic acid hydrazide, dimethylaminoacetyldrazide or the like. The reaction is carried out in the presence of N,N-dimethyl-p-toluidine, or N-ethyldiisopropylamine or even without a base and is heated under reflux in chlorobenzene or p-xylene for some hours.

In accordance with process variant b) compounds of formula I may be prepared in the following way: A compound of formula IV, for example 6,8-dibromo-4H-2,5,10b-triaza-benzo[e]azulene-3-carboxylic acid ethyl ester or 6-bromo-3-(3-cyclopropyl-[1,2,4]oxadiazol-5-yl)-8-methylsulfanyl-4H-2,5,10b-triaza-benzo[e]azulene is treated with an anhydrous solution of hydrazine. A suitable solvent is THF. The resulting mixture is heated for some hours. After cooling and evaporation the solid may directly used in the next step. The obtained solid is then treated with a corresponding compound of formula VI, for example with triethyl orthoformate in an alcohol, such as ethanol. The mixture is heated under reflux for several hours.

The salt formation is effected at room temperature in accordance with methods which are known per se and which are familiar to any person skilled in the art. Not only salts with inorganic acids, but also salts with organic acids are possible. Hydrochlorides, hydrobromides, sulphates, nitrates, citrates, acetates, maleates, succinates, methanesulphonates, p-toluenesulphonates and the like are examples of such salts.

The following scheme 1 describes the processes for preparation of compounds of formula I in more detail. The starting materials are known compounds or may be prepared according to methods known in the art, for example in accordance with schemes 2, 3 and 4.

Scheme 1

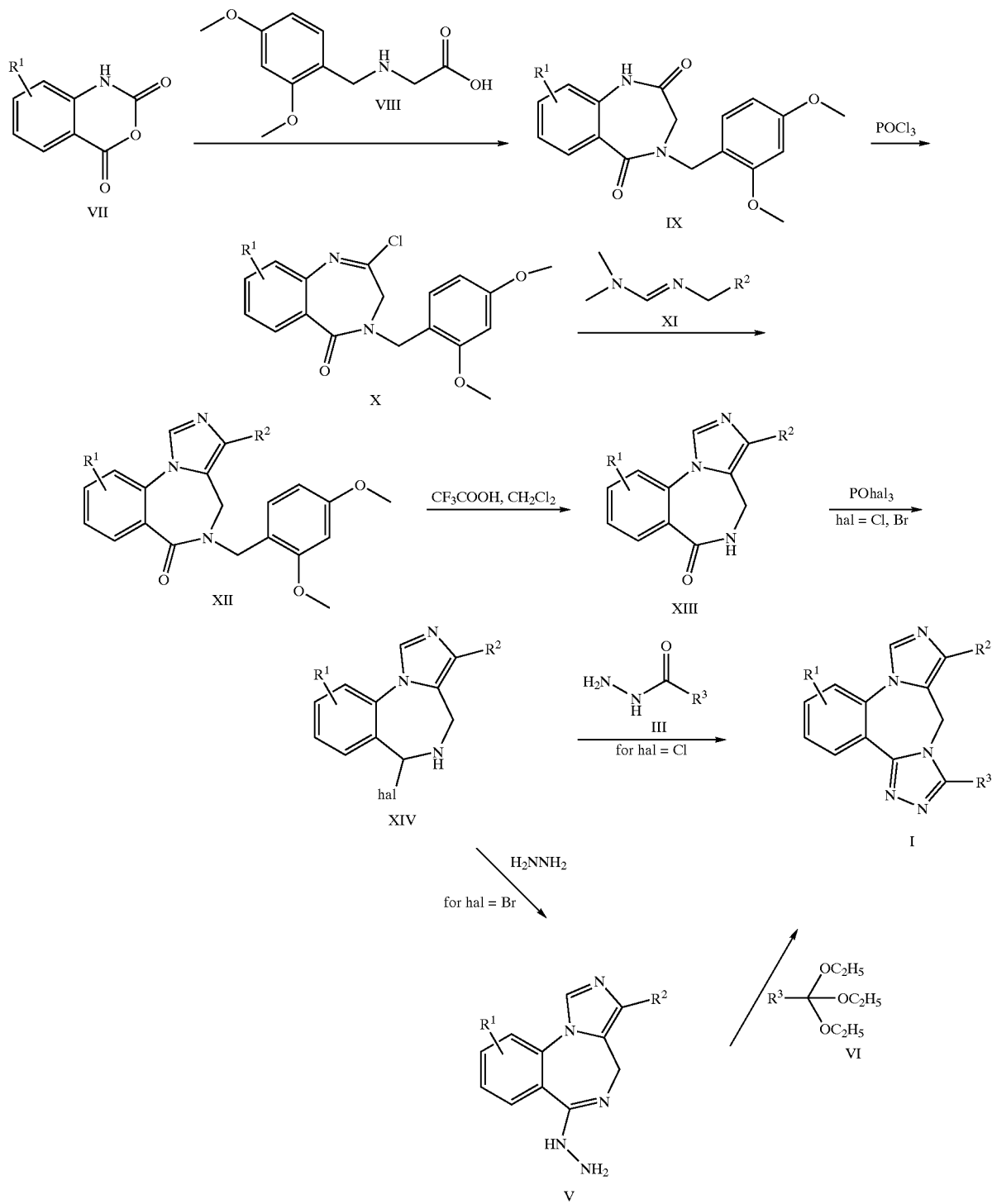

The substituents given in scheme 1 are described above.

In accordance with scheme 1 a compound of formula I may be prepared as follows: A corresponding compound of formula VII, a $R^1$-substituted 2H-3,1 benzoxazine-2,4(1H)-dione, and (2,4-dimethoxy-benzylamino)-acetic acid (VIII) is suspended in p-xylene and is heated under argon for about 2 hours. After cooling to room temperature, a spontaneous crystallization occurred. The obtained compound of formula IX is solved in toluene in the presence of N,N-dimethyl-p-toluidine. Then phosphorous oxide chloride is added and the solution is heated and after completion of the reaction toluene is evaporated. The obtained compound of formula X is then dissolved in TIF and added to a mixture of a cooled solution of lithium diisopropylamide in TBF and of (E)-(dimethylamino-methyleneamino)-acetic acid ethyl ester or of (E/Z)-N'(3-cyclopropyl-[1,2,4]oxadiazol-5-yl-methyldimethyl-formamidine. In a further step the obtained compound of formula XII is dissolved in a mixture of $CH_2Cl_2$ and trifluoroacetic acid and then treated with trifluoromethanesulfonic acid. The obtained compound of formula XIII is purified in conventional manner. A mixture of this compound and N,N-dimethyl-p-toluidine is dissolved in chlorobenzene under argon and phosphorous oxide chloride or bromide is then added at room temperature and the mixture is heated at reflux. The obtained compound of formula XIV is purified by known methods. If "hal" in formula XIV is chlorine, a compound of formula I may be obtained by reaction of a compound of formula XIV, for example the compound 6-chloro-8-methoxy-4H-2,510b-triaza-benzo[e]azulene-3-carboxylic acid ethyl ester, with a corresponding formylhydrazine of formula III. The reaction is carried out in the presence of N,N-dimethyl-p-toluidine, or N-ethyldiisopropylamine or even without a base and is heated in chlorobenzene or p-xylene under reflux. If "hal" in formula XIV is bromine, a compound of this formula, for example 6,8-dibromo-4H-2,510b-triaza-benzo[e]azulene-3-carboxylic acid ethyl ester, is treated with an anhydrous solution of hydrazine and the obtained solid compound of formula V may directly used in the last reaction step. Finally, a compound of formula I is obtained by heating under reflux a mixture of a compound of formula V in ethanol, containing triethylorthoformate.

Preparation of the Starting Materials

Scheme 2

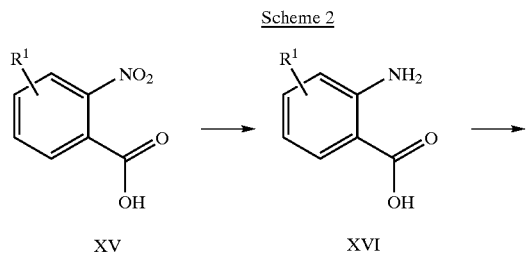

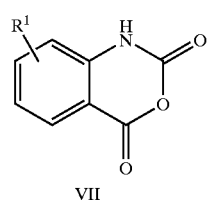

VII $R^1$ in scheme 2 has the significance given above.

In accordance with scheme 2 the starting material of formula VII is prepared. A compound of formula XV is hydrogenated in conventional manner to the corresponding 2-amino-benzoic acid of formula XVI. This compound is then dissolved in dioxane and treated with bis(trichloromethyl)carbonate under reflux.

Scheme 3

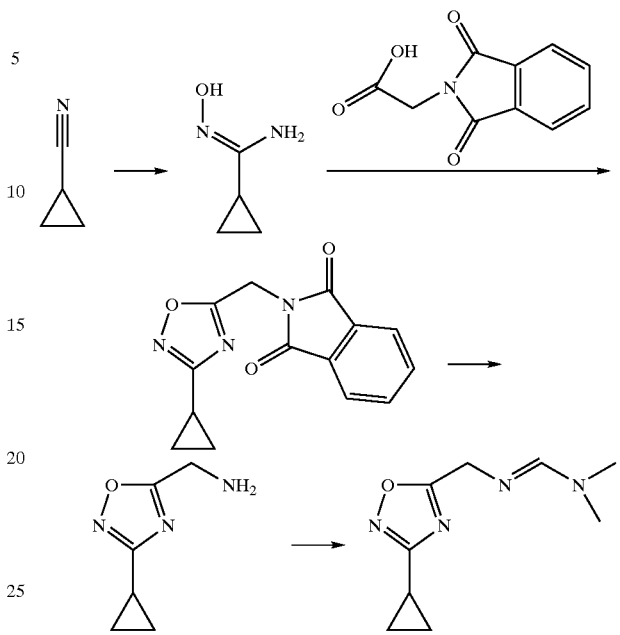

Scheme 3 describes the preparation of known starting materials. The processes for preparation of these compounds are also known or may be carried out in analogous manner to known methods. For example, N-[(3-cyclopropyl-1,2,4-oxadiazol-5-yl)methyl]phthalimide is prepared by reaction of N-phthaloylglycine in DMF and 1,1'carbonyldiimidazole, and followed by the addition of cyclopropanecarboxamidoxime. The obtained N-[(3-cyclopropyl-1,2,4-oxadiazol-5-yl)methyl]phthalimide is then dissolved in 1,2-dichloroethane and N-methylhydrazine is added. The obtained 4-(aminomethyl)-3-cyclopropyl-1,2,4-oxadiazole is then treated with N,N-dimethylformaldehyde diethyl acetal and heated at about 130° C. and the desired starting material (E/Z)-N'-(3-cyclopropyl-[1,2,4]oxadiazol-5-ylmethyl-N,N-dimethyl-formamidine is obtained.

Scheme 4

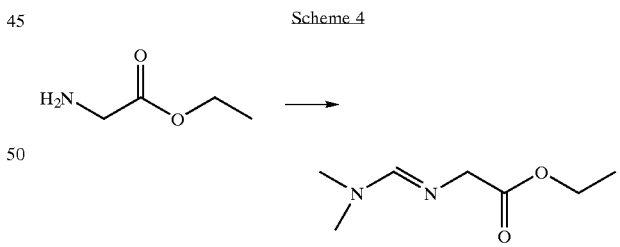

In accordance with scheme 4 the starting material (E)-(dimethylamino-methyleneamino)-acetic ethyl ester may be prepared from a mixture of glycine and N,N-dimethylformamide diethylacetal in ethanol.

As mentioned earlier, the compounds of formula I and their pharmaceutically usable salts possess valuable pharmacological properties. It has been found that the compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [$^3$H]flumazenil (85 Ci/mmol; Amersham) binding to SF9 cells expressing rat receptors of composition α1β3γ2, α2β3γ2, α3β3γ2 and α5β3γ2.

Cellpellets were suspended in Krebs-tris buffer (4.8 mM KCl, 1.2 mM CaCl$_2$, 1.2 mM MgCl$_2$, 120 mM NaCl, 15 mM Tris; pH 7.5; binding assay buffer), homogenized by polytron for ca. 15 sec on ice and centrifuged in UZ for 30 min at 4° C. (100000 g; rotor: TFT 4594=300000 rpm). The cellpellets were resuspended in Krebs-tris buffer and homogenized by polytron for ca. 15 sec on ice. Aliquots of 1 ml were prepared, protein was measured (Bradford method) and the resulting membrane aliquots were stored at −70° C.

Radioligand binding assays were carried out in a volume of 200 μL (96-well plates) which contained 100 μL of cells, [$^3$H]flumazenil at a concentration of 1 nM for α1α2α3 subunits and 0.5 nM for α5 subunits and the test compound in the range of $10^{-10}$–$3\times10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and all were found to possess a Ki value for displacement of [$^3$H]flumazenil from α5 subunits of the rat GABA A receptor of 100 nM or less. In a preferred embodiment the compounds of the invention are binding selective for the α5 subunit relative to the α1, α2 and α3 subunit.

In the table below it is shown the activity data of some preferred compounds:

| Example No. | Ki[nM] ra1 | Ki[nM] ra2 | Ki[nM] ra3 | Ki[nM] ra5 |
|---|---|---|---|---|
| 1 | 30.6 | 57.6 | 39.2 | 1.3 |
| 6 | 407.8 | 361.5 | 148.8 | 10.8 |
| 13 | 34.9 | 55.5 | 23.7 | 1.2 |
| 19 | 480.9 | 500.1 | 482.3 | 14.5 |
| 20 | 802.7 | 283.9 | 190.9 | 10.7 |
| 25 | 95.3 | 122.8 | 107.4 | 5.9 |
| 37 | 295.8 | 266.1 | 162.0 | 8.2 |
| 47 | 694.5 | 224.6 | 100.3 | 13.1 |
| 50 | 1002.9 | 409.4 | 220.1 | 14.4 |
| 54 | 64.6 | 148.0 | 108.2 | 12.9 |
| 69 | 359.8 | 308.4 | 158.1 | 7.0 |
| 61 | 67.3 | 53.0 | 18.9 | 1.3 |
| 63 | 12.5 | 10.7 | 5.6 | 0.6 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragées and hard gelatin capsules. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following examples illustrate the present invention without limiting it. All temperatures are given in degrees Celsius.

Intermediate A (2,4-Dimethoxy-benzylamino)-acetic Acid

This intermediate is known[1] and may be prepared by methods, known in the art, for example in the following way:

Glycine (100 g, 1.33 mol) was dissolved in 1 N NaOH (1.6 L) and treated with a solution of 2,4-dimethoxybenzaldehyde (200 g, 1.20 mol) in MeOH (800 mL).

The resulting solution was hydrogenated over 10% Pd/C (40 g) at 1.1 bar H$_2$ for 2 h at room temperature (rt). The catalyst was filtered off and washed with MeOH (500 mL). The filtrate was concentrated to ca. 2 L by distilling off all the MeOH.

The resulting basic aqueous solution was cooled in ice, and acidified to pH 4 with 3 N HCl (ca. 500 mL), causing the product to precipitate. The white solid was filtered off, and washed with ice water (200 mL). The wet crystals were dried at 60° C., first at 25 mbar overnight, then at 0.1 mbar for 8 h. One obtained 232 g (85%), which was contaminated with 3% NaCl, but was used without further purification. mp 115° C. m/z 225 (M).

Intermediate B (E)-(Dimethylamino-methyleneamino)-acetic Acid Ethyl ester

This intermediate is known[2] and may be prepared by methods, known in the art, for example in the following ways:

Method A

A mixture of glycine (69.8 mL, 0.8 mol) and N,N-dimethylformamide diethylacetal (69.8 mL, 4.0 mol) was heated under reflux and the ethanol formed was removed by means of a Dean-Stark trap. Distillation. Yield: 108.4 g (86%): bp 120–122° C. 128 mbar.

Method B

Gycine ethyl ester HCl was dissolved in portions in 10% aqueous $Na_2CO_3$. The resulting solution was saturated with NaCl, filtered, and the filtrate extracted twice with $CH_2Cl_2$ (400 mL). The organic layer was dried, filtered and carefully evaporated. The residue was distilled at 45° C./18 mbar. One obtained glycine ethyl ester (32 g, 43%) as a colorless liquid.

Glycine ethyl ester (35 g, 339 mmol) was dissolved in N,N-dimethylformamide diethyl acetal (64 mL, 373 mL) and heated to 130° C. Ethanol (ca. 20 mL) was distilled off by means of a Dean-Stark trap. The residue was distilled at 110° C./18 mbar. One obtained a yellowish liquid (52 g, 97%). m/z 159 (M+H).

Intermediate C (E/Z)-N'-(3-Cyclopropyl-[1,2,4]oxadiazol-5-ylmethyl)-N,N-dimethyl-formamidine Step 1

N-[(3-Cyclopropyl-1,2,4-oxadiazol-5-yl)methyl]phthalimide

N-Phthaloylglycine (90.7 g, 442 mmol) was dissolved in portions (because of clumping) in DMF (500 mL). 1,1'-Carbonyldiimidazole (78.9 g, 486 mmrol) was added in portions (attention CO evolution). The resulting suspension was heated at 80° C. for 20 min. and then cooled to rt, then cyclopropanecarboxamidoxime [1] added and then heated at 110° C. for 2 h. The solution was cooled to rt, then poured into water (4 L), stirred for 15 min, filtered, washed with water (400 mL) and (fried. Yield: 104 g (87%). Mp 115° C. m/z 269 (M).

Step 2

4-(Aminomethyl)-3-cyclopropyl-1,2,4-oxadiazole

N-[(3-Cyclopropyl-1,2,4-oxadiazol-5-yl)methyl]phthalimide (104 g, 387 mmol) was dissolved in 1,2-dichloroethane (500 mL), N-methylhydrazine (22.4 mL, 426 mmol) was added and the solution was refluxed for 5 h. The suspension was cooled in ice, the precipitate (2-methyl-2,3-dihydro-phthalazine-1,4-dione) was filtered off and washed with 1,2-dichloroethane (100 mL). The filtrate was evaporated and the residue distilled at 70° C./0.4 mbar (bath-T 100–150° C). Yield: 39.3 g (73%). m/z 139 (M).

Step 3

(E/Z)-N'-(3-Cyclopropyl-[1,2,4]oxadiazol-5-ylmethyl)-N,N-dimethyl-formamidine 4-(Aminomethyl)-3-cyclopropyl-1,2,4-oxadiazole (39.3 g, 282 mmol) was dissolved in N,N-dimethylformaldehyde diethyl acetal (77 mL, 451 mmol) and heated at 130° C. until all liberated EtOH had distilled off (Hickmann condenser). Vacuum was then applied to remove first the excess reagent and then the product was distilled at 140–150° C. bath-T/0.1 mbar. Yield: 49.3 g (90%). m/z 195 (MH+).

EXAMPLE 1

Ethyl 3-methoxy-9H-imidazo[1,5-a][1,2,4]triazolo[4,3-d][1,4]-benzodiazepine-10-carboxylate Step 1

6-Methoxy-2H-3,1-benzoxazine-2,4(1H)-dione

This intermediate is known[3] and may be prepared by methods, known in the art, for example in the following way:

2-Amino-5-methoxybenzoic acid (19.3 g, 115 mmol) was dissolved in dioxane (200 mL), treated with bis(trichloromethyl)carbonate (11.3 g, 38 mmol) and refluxed for 1 h. The suspension was cooled to rt, the crystals filtered off and washed with dioxane (20 mL). The mother liquor was evaporated and the residue crystallized from ethyl acetate. Yield: 20.9 g (94%). mp 244° C. (dec). m/z 193 (M).

Step 2

4-(2,4-Dimethoxy-benzyl)-7-methoxy-3,4-dihydro-1H-benzo[e][1,4]diazepine-2,5-dione 6-Methoxy-2H-3,1-benzoxazine-2,4(1H)-dione (23 g, 119 mmol) and (2,4-dimethoxy-benzylamino)-acetic acid [1] (27 g, 120 mmol) were suspended in p-xylene (500 mL) and heated under argon at reflux (140° C.) for 2 h. The hot solution was allowed to cool to rt, while spontaneous crystallization occurred. The crystals were filtered off and washed with p-xylene (50 mL). Yield: 39 g (92%). mp 196° C. m/z 356 (M).

Step 3

2-Chloro-4-(2,4-dimethoxy-benzyl)-7-methoxy-3,4-dihydro-benzo[e][1,4]diazepin-5-one 4-(2,4-Dimethoxy-benzyl)-7-methoxy-3,4-dihydro-1H-benzo[e][1,4]diazepine-2,5-dione (23.7 g, 67 mmol) and N,N-dimethyl-p-toluidine (19.2 mL, 133 mmol) were mixed in toluene (200 mL) and heated to 100° C. Then phosphorous oxide chloride (6.7 mL, 73 mmol) was added dropwise and heating at 100° C. was continued for 2.5 h. The resulting dark red solution was evaporated to dryness and the residue redissolved in THF (150 mL) and used directly in the subsequent step.

Step 4

5-(2,4-Dimethoxy-benzyl)-8-methoxy-6-oxo-5,6-dihydro-4H-2,5,10b-triaza-benzo[e]azulene-3-carboxylic Acid Ethyl Ester Hexamethyldisilazane (48.5 mL, 66 mmol) was dissolved in TBF (150 mL), cooled under argon to −70° C., and treated slowly with a 1.6 M solution of n-butyllithium in hexane (145 ml, 233 mmol). After stirring for 1 h at −70° C., a solution of (E)-(dimethylamino-methyleneamino)-acetic acid ethyl ester (21 g, 133 mmol) in THF (50 mL) was added, and stirring continued for 1 h at −70° C. Then a solution of 2-chloro-4-(2,4-dimethoxy-benzyl)-7-methoxy-3,4-dihydro-benzo[e][1,4]diazepin-5-one (24.9 g, 66 mmol) in TBF (150 mL) was added at −70° C., and subsequently allowed to warm to 10° C. over ca. 1 h, then cooled again to −30° C. Neat acetic acid (38 mL, 664 mmol) was added slowly at −30° C. with cooling, the muddy suspension was allowed to warm to 0° C., water (40 mL) added, and the resulting solution was refluxed for 1 h, leading to the formation of a thick precipitate. The hot suspension was diluted with water (450 mL), cooled to 30° C., filtered, and the white crystals washed with THF/water 1:1 (400 mL), and dried at 25 mbar/60° C. Yield: 16.7 g (56%). mp 204° C. m/z 451 (M).

Step 5

8-Methoxy-6-oxo-5,6-dihydro-4H-2,5,10b-triaza-benzo[e]azulene-3-carboxylic Acid Ethyl Ester 5-(2,4-Dimethoxy-benzyl)-8-methoxy-6-oxo-5,6-dihydro-4H-2,5,10b-triaza-benzo[e]azulene-3-carboxylic acid ethyl ester (9.8 g, 22 mmol) was suspended in $CH_2Cl_2$ (50 mL), cooled in ice, and diluted sowly with trifluoroacetic acid (50 mL). The resulting clear solution was treated at 5° C. with trifluoromethanesulfonic acid (3.8 mL, 44 mmol). The now red solution was stirred at rt for 2 h, evaporated to dryness, and the residue extracted with $CH_2Cl_2$ (500 mL), and 2×10% $NaHCO_3$ (500 mL). The crude product (ca. 10 g) was digested with hot ethyl acetate (100 mL), allowed to cool, and the white crystals (5.6 g, 85%) were filtered off. mp 240° C. m/z 301 (M).

Step 6
6-Chloro-8-methoxy-4H-2,5,10b-triaza-benzo[e]azulene-3-carboxylic Acid Ethyl Ester 8-Methoxy-6-oxo-5,6-dihydro-4H-2,5,10b-triaza-benzo[e]azulene-3-carboxylic acid ethyl ester (7.5 g, 25 mmol) and N,N-dimethyl-p-toluidine (10.8 mL, 75 mmol) were mixed in chlorobenzene (80 mL) under argon. Phosphorous oxide chloride (3.4 mL, 37 mmol) was added at rt, and the mixture heated at reflux for 3.5 h. The resulting solution was cooled to rt, diluted with $CH_2Cl_2$/aceton 100:15 (300 mL), and directly purified by flash chromatography on silica gel in $CH_2Cl_2$/acetone 100:15. The white product was recrystallized by dissolution in hot ethyl acetate (300 mL), concentrated until precipitation started (ca. 100 mL). Yield: 7 g (88%). mp 186° C. m/z 301 (M).

Step 7
Ethyl 3-methoxy-9H-imidazo[1,5-a][1,2,4]triazolo[4,3-d][1,4]-benzodiazepine-10-Carboxylate 6-Chloro-8-methoxy-4H-2,5,10b-triaza-benzo[e]azulene-3-carboxylic acid ethyl ester (0.1 g, 0.31 mmol), formylhydrazine (41 mg, 0.69 mmol), and N-ethyldiisopropylamine 0.054 mL, 0.31 mmol) were refluxed in chlorobenzene (1 mL) for 4 h. The reaction mixture was extracted with $CH_2Cl_2$/water, the organic layer was dried and evaporated. The residue was purified by chromatography on silica gel in $CH_2Cl_2$/MeOH 30:1. mp 197° C. m/z 325 (M).

EXAMPLE 2
Ethyl 3-methyl-9H-imidazo[1,5-a][1,2,4]triazolo[3,4-d][1,4]benzodiazepine-10-Carboxylate Step 1
6-Methyl-2H-3,1-benzoxazine-2,4(1H)-dione This intermediate is known and may be prepared by methods, known in the art, for example in the following way:

A mixture of 2-amino-5-methylbenzoic acid (45.2 g, 0.30 mol) and ethyl chloroformate (31.4 mL, 0.33 mol) in dioxane (250 mL) was heated under reflux for 4.5 h. After cooling, acetyl chloride (50 mL) was added and heating under reflux continued for another 4 h. After cooling, the mixture was evaporated and the resulting solid digested with tert-butyl methyl ether: heptane (1:1, 400 mL) by heating under reflux for 1 h. The soild was then filtered off and washed with tert-butyl methyl ether: heptane (1:1, 80 mL). Yield: 47.7 g (90%). m/z 177 (M).

Step 2
4-(2,4-Dimethoxy-benzyl)-7-methyl-3,4-dihydro-1H-benzo[e][1,4]diazepine-2,5-dione A suspension of 6-methyl-2H-3,1-bezoxazine-2,4(1H)-dione (18.3 g, 103 mmol) containing (2,4-dimethoxybenzylamino)-acetic acid (25.6 g, 114 mmol) in p-xylene (125 mL) was heated under reflux (150° C.) for 2.5 h. After cooling to room temperature the precipitate was filtered off and washed with p-xylene (2×20 ml). Yield: 34.1 g (97%). m/z 341 (MH⁺).

Step 3
2-Chloro-4-(2,4-dimethoxy-benzyl)-7-methyl-3,4-dihydro-benzo[e][1,4]diazepin-5-one 4-(2,4-Dimethoxy-benzyl)-7-methyl-3,4-dihydro-1H-benzo[e][1,4]diazepine-2,5-dione (34.0 g, 100 mmol) and N,N-dimethyl-p-toluidine (28.9 mL, 200 mmol) were mixed in toluene (100 mL) and heated to 100° C. Then phosphorus oxychloride (10.1 mL, 110 mmol) was added dropwise and heating at 100° C. was continued for 2.5 h. The resulting dark red solution was used directly in the subsequent step.

Step 4
5-(2,4-Dimethoxy-benzyl)-8-methyl-6-oxo-5,6-dihydro-4H-2,5,10b-triaza-benzo[e]azulene-3-carboxylic Acid Ethyl Ester Hexamethyldisilazane (68.7 mL, 330 mmol) was dissolved in THF (350 mL), cooled under Argon to −70° C., and treated slowly with a 1.6 M solution of n-BuLi in hexane (206 mL, 330 mmol). After stirring for 1 h at −70° C., a solution of (E)-(dimethylamino-methyleneamino)-acetic acid ethyl ester (31.6 g, 200 mmol) in THF (30 mL) was added, and stirring continued for 1 h at −70° C. Then a solution of 2-chloro-4-(2,4-dimethoxy-benzyl)-7-methyl-3,4-dihydro-benzo[e][1,4]diazepin-5-one (35.9 g, 100 mmol) (prepared as described above) was added at −70° C., and subsequently allowed to warm up to at 10° C. over 1 h, then cooled again to −30° C. After 30 min, acetic acid (57 mL) was added at −30° C. and the suspension was allowed to warm up to room temperature and water (57 mL) added and the resulting mixture heated under reflux for 14 h. After cooling, the mixture was evaporated and then dissolved in DCM (300 mL). This solution was then washed with HCl (1 M, 2×100 mL) and 10% sodium hydrogen carbonate (100 ml), dried ($Na_2SO_4$) and evaporated. Chromatography on silica gel eluting with EtOAc. Yield: 17.6 g (41%). m/z 436 (MH⁺).

Step 5
8-Methyl-6-oxo-5,6-dihydro-4H-2,5,10b-triaza-benzo[e]azulene-3-carboxylic Acid Ethyl Ester 5-(2,4-Dimethoxy-benzyl)-8-methyl-6-oxo-5,6-dihydro-4H-2,5,10b-triaza-benzo[e]azulene-3-carboxylic acid ethyl ester (9.8 g, 23 mmol) was suspended in $CH_2Cl_2$ (100 mL), cooled in ice, and diluted slowly with trifluroacetic acid (30 mL). The resulting solution was treated at 5° C. with trifluoromethanesulfonic acid (3.0 mL, 34 mmol). The red solution was stirred at room temperature for 2 h. The mixture was then evaporated and dissolved in $CH_2Cl_2$ (20 mL), washed with 10% sodium hydrogen carbonate (2×5 mL) and the organic layer was dried ($Na_2SO_4$) and evaporated. Trituration with EtOAc. Yield: 9.55 g (92%). m/z 283 (M—H⁻).

Step 6 and Step 7 (without isolation of 6-chloro-8-methyl-4H-2,5,10b-triaza-benzo[e]azulene-3-carboxylic Acid Ethyl Ester)

6-Chloro-8-methyl-4H-2,5,10b-triaza-benzo[e]azulene-3-carboxylic Acid Ethyl Ester and Ethyl 3-methyl-9H-imidazo[1,5-a][1,2,4]triazolo[3,4-d][1,4]benzodiazepine-10-Carboxylate 8-Methyl-6-oxo-5,6-dihydro-4H-2,5,10b-triaza-benzo[e]azulene-3-carboxylic acid ethyl ester (9.5 g, 33 mmol) and N,N-dimethyl-p-toluidine (14.4 ml, 99 mmol) were mixed in chlorobenzene (100 mL) under argon. Phosphorous oxychloride (4.6 mL, 50 mmol) was added at room temperature and the resulting mixture heated under reflux for 1.5 h. After cooling, the mixture was evaporated and used in the subsequent step. The mixture was dissolved in chlorobenzene (100 mL) and then N,N-ethyldiisopropylamine (5.7 mL, 33 mmol) and formylhydrazine (4.4 g, 66 mmol) added and the resulting mixture heated under reflux for 4 h. After cooling, the mixture was evaporated and dissolved in $CH_2Cl_2$ (50 mL) and water (20 mL). The organic layer was separated, dried ($Na_2SO_4$) and evaporated. Chromatography on silica gel eluting with EtOAc. Yield: 2.85 g (28%). m/z 310 (MH⁺). mp 236–238° C.

EXAMPLE 3

Ethyl-3-isopropyl-9H-imidazo[1,5-a][1,2,4]triazolo[4,3-d][1,4]-benzodiazepine-10-carboxylate Step 1
6-Isopropyl-1H-benzo[d][1,3]oxazine-2,4-dione A mixture of 2-amino-5-isopropylbenzoic acid (30. g, 16.7 mmol) and ethyl chloroformate (1.75 mL, 18.4 mmol) in dioxane (20 mL) was heated under reflux for 2 h. After cooling, acetyl chloride (1.4 mL) was added and heating under reflux continued for another 3 h. After cooling, the mixture was evaporated and the resulting solid digested with tert-butyl methyl ether: heptane (1:1, 20 mL) by heating under reflux for 1 h. The soild was then filtered off and washed with tert-butyl methyl ether: heptane (1:1, 10 mL). Yield 3.1 g (89%). m/z 204 (M—H$^-$).

Step 2
4-(2,4-Dimethoxy-benzyl)-7-isopropyl-3,4-dihydro-1H-benzo[e][1,4]diazepine-2,5-dione A suspension of 6-isopropyl-1H-benzo[d][1,3]oxazine-2,4-dione (3.0 g, 15 mmol) containing (2,4-dimethoxy-benzylamino)-acetic acid (3.7 g, 16 mmol) in p-xylene (40 mL) was heated under reflux (150° C.) for 2.5 h. After cooling to room temperature the precipitate was filtered off and washed with p-xylene (2×20 ml). Yield: 4.9 g (90%). m/z 367 (M—H$^-$).

Step 3
2-Chloro-4-(2,4-dimethoxy-benzyl)-7-isopropyl-3,4-dihydro-benzo[e][1,4]diazepin-5-one 4-(2,4-Dimethoxy-benzyl)-7-isopropyl-3,4-dihydro-1H-benzo[e][1,4]diazepine-2,5-dione (1.5 g, 4.1 mmol) and N,N-dimethyl-p-toluidine (1.76 mL, 12.2 mmol) were mixed in toluene (8 mL) and heated to 100° C. Then phosphorus oxychloride (559 µL, 6.1 mmol) was added dropwise and heating at 100° C. was continued for 2.5 h. After cooling, the mixture was evaporated and dissolved in THF (10 mL) and was used directly in the subsequent step.

Step 4
5-(2,4-Dimethoxy-benzyl)-8-isopropyl-6-oxo-5,6-dihydro-4H-2,5,10b-triaza-benzo[e]azulene-3-carboxylic Acid Ethyl Ester Hexamethyldisilazane (2.8 mL, 13.4 mmol) was dissolved in TBF (25 mL), cooled under Argon to −70° C., and treated slowly with a 1.6 M solution of n-BuLi in hexane (8.4 mL, 13.4 mmol). After stirring for 1 h at −70° C., a solution of (E)-(dimethylamino-methyleneamino)-acetic acid ethyl ester (1.28 g, 8.1 mmol) in THF (5 mL) was added, and stirring continued for 1 h at −70° C. Then a solution of 2-chloro-4-(2,4-dimethoxy-benzyl)-7-isopropyl-3,4-dihydro-benzo[e][1,4]diazepin-5-one (1.59 g, 4.1 mmol) (prepared as described above) was added at −70° C., and subsequently allowed to warm up to at 10° C. over 1 h, then cooled again to −30° C. After 30 min, acetic acid (3.0 mL) was added at −30° C. and the suspension was allowed to warm up to room temperature and water (3.0 mL) added and the resulting mixture heated under reflux for 14 h. After cooling, the mixture was evaporated and then dissolved in DCM (30 mL). This solution was then washed with HCl (1 M, 2×15 mL) and sodium hydrogen carbonate (sat., 10 ml), dried (Na$_2$SO$_4$) and evaporated. Chromatography on silica gel eluting with EtOAc:Hexane (19:1). Yield: 1.9 g (99%). m/z 464 (MH$^+$).

Step 5
8-Isopropyl-6-oxo-5,6-dihydro-4H-2,5,10b-triaza-benzo[e]azulene-3-carboxylic Acid Ethyl Ester 5-(2,4-Dimethoxy-benzyl)-8-isopropyl-6-oxo-5,6-dihydro-4H-2,5,10b-triaza-benzo[e]azulene-3-carboxylic acid ethyl ester (410 mg, 0.9 mmol) was suspended in CH$_2$Cl$_2$ (3.0 mL), cooled in ice, and diluted slowly with trifluoroacetic acid (2.0 mL). The resulting solution was treated at 5° C. with trifluoromethanesulfonic acid (1.0 mL, 1.3 mmol). The red solution was stirred at room temperature for 2 h. The mixture was then evaporated and dissolved in CH$_2$Cl$_2$ (20 mL), washed with sodium hydrogen carbonate (10%, 2×5 mL) and the organic layer was dried (Na$_2$SO$_4$) and evaporated. Trituration with EtOAc. Yield: 250 mg (90%). m/z 313 (MH).

Step 6
6-Chloro-8-isopropyl-4H-2,5-10b-triaza-benzo[e]azulene-3-carboxylic Acid Ethyl Ester 8-Isopropyl-6-oxo-5,6-dihydro-4H-2,5,10b-triaza-benzo[e]azulene-3-carboxylic acid ethyl ester (1.8 g, 5.6 mmol) and N,N-dimethyl-p-toluidine (2.4 mL, 16.9 mmol) were mixed in chlorobenzene (10 mL) under argon. Phosphorus oxychloride (771 µL, 8.4 mmol) was added at room temperature and the resulting mixture heated under reflux for 2 h. After cooling, the mixture was evaporated. Chromatography on silica gel eluting with EtOAc. Yield: 1.3 g (68%).

Step 7
Ethyl-3-isopropyl-9H-imidazo[1,5-a][1,2,4]triazolo[4,3-d][1,4]-benzodiazepin-10-carboxylate 6-Chloro-8-isopropyl-4H-2,5,10b-triaza-benzo[e]azulene-3-carboxylic acid ethyl ester (50 mg, 0.15 mmol), formylhydrazine (10 mg, 0.17 mmol), and N,N-dimethyl-p-toluidine (24 µL, 0.17 mmol) were heated under reflux in chlorobenzene (2 mL) for 10 h. The reaction mixture was then evaporated. Chromatography by preparative HPLC. Yield 8.7 mg (17%) m/z 338 (M) mp 160–163° C.

EXAMPLE 4 (Method A)

Ethyl 3-bromo-9H-imidazo[1,5-a][1,2,4]triazolo[4,3-d][1,4]-benzodiazepine-10-carboxylate Step 1
4-(2,4-Dimethoxy-benzyl)-7-bromo-3,4-dihydro-1H-benzo[e][1,4]diazepine-2,5-dione A suspension of 6-bromo-2H-3,1-bezoxazine-2,4(1H)-dione (22.0 g, 91 mmol) containing (2,4-dimethoxy-benzylamino)-acetic acid (22.5 g, 100 mmol) in p-xylene (200 mL) was heated under reflux (150° C.) for 1 h. After cooling to room temperature the precipitate was filtered off and washed with p-xylene (100 ml). Yield: 33.5 g (91%) m/z 403/405 (M).

Step 2
2-Chloro-4-(2,4-dimethoxy-benzyl)-7-bromo-3,4-dihydro-benzo[e][1,4]diazepin-5-one 4-(2,4-Dimethoxy-benzyl)-7-bromo-3,4-dihydro-1H-benzo[e][1,4]diazepine-2,5-dione (3.0 g, 7.4 mmol) and N,N-dimethyl-p-toluidine (2.1 mL, 14.8 mmol) were mixed in toluene (30 mL) and heated to 100° C. Then phosphorus oxychloride (745 µL, 8.1 mmol) was added dropwise and heating at 100° C. was continued for 2.5 h. The resulting dark red solution was evaporated and the residue dissolved in THF (10 mL) and used directly in the subsequent step.

Step 3
5-(2,4-Dimethoxy-benzyl)-8-bromo-6-oxo-5,6-dihydro-4H-2,5,10b-triaza-benzo[e]azulene-3-carboxylic Acid Ethyl Ester Hexamethyldisilazane (5.1 mL, 24.4 mmol) was dissolved in TBF (30 mL), cooled under Argon to −70° C., and treated slowly with a 1.6 M solution of n-BuLi in hexane (14.5 mL, 23.2 mmol). After stirring for 1 h at −70° C., a solution of (E)-(dimethylamino-methyleneamino)-acetic acid ethyl ester (2.34 g, 14.8 mmol) in THF (10 mL) was added, and stirring continued for 1 h at −70° C. Then a solution of 2-chloro-4-(2,4-dimethoxy-benzyl)-7-bromo-3, 4-dihydro-benzo[e][1,4]diazepin-5-one (3.1 g, 7.4 mmol) in THF (10 mL) (prepared as described above) was added at −70° C., and subsequently allowed to warm up to at 10° C. over 1 h, then cooled again to −30° C. After 30 min, acetic acid (8 mL) was added at −30° C. and the suspension was allowed to warm up to room temperature and water (8 mL) added and the resulting mixture heated under reflux for 2 h. After cooling, the mixture was evaporated and then dissolved in DCM (30 mL). This solution was then washed with HCl (1 M, 2×15 mL) and sodium hydrogen carbonate (sat., 10 ml), dried ($Na_2SO_4$) and evaporated. Chromatography on silica gel eluting with EtOAc. Yield: 0.9 g (24%). m/z 500/502 (M).

Step 4
8-Bromo-6-oxo-5,6-dihydro-4H-2,5,10b-triaza-benzo[e]azulene-3-carboxylic Acid Ethyl Ester 5-(2,4-Dimethoxy-benzyl)-8-bromo-6-oxo-5,6-dihydro-4H-2,5,10b-triaza-benzo[e]azulene-3-carboxylic acid ethyl ester (2.6 g, 5.2 mmol) was suspended in $CH_2Cl_2$ (15 mL), cooled in ice, and diluted slowly with trifluoroacetic acid (11.9 mL). The resulting solution was treated at 5° C. with trifluoromethanesulfonic acid (680 μL, 7.8 mmol). The red solution was stirred at room temperature for 1.5 h. The mixture was then evaporated and dissolved in $CH_2Cl_2$ (50 mL), washed with sodium hydrogen carbonate (10%, 2×25 mL) and the organic layer was dried ($Na_2SO_4$) and evaporated. Trituration with EtOAc. Yield: 1.8 g (100%). m/z 350/352 (M).

Steps 5 and 6
6,8-Dibromo-4H-2,5-10b-triaza-benzo[e]azulene-3-carboxylic Acid Ethyl Ester and 8-bromo-6-hydrazino-4H-2,5,10b-triaza-benzo[e]azulene-3-carboxylic Acid Ethyl Ester 8-Bromo-6-oxo-5,6-dihydro-4H-2,5,10b-triaza-benzo[e]azulene-3-carboxylic acid ethyl ester (0.2 g, 0.6 mmol) and N,N-dimethyl-p-toluidine (165 μL, 1.1 mmol) were mixed in toluene (5 mL), treated with phosphoryl bromide (180 mg, 0.6 mmol) and refluxed for 5 h. After cooling, the mixture was evaporated and the residue was extracted with $CH_2Cl_2$ (10 mL) and water (10 mL). The organic layer was separated, dried ($Na_2SO_4$) and then evaporated. The residue was dissolved in THF (10 mL) and treated with an anhydrous solution of hydrazine (1 M, in THF, 2.0 mL, 0.2 mmol) and the resulting mixture heated under reflux for 12 h. After cooling the mixture was evaporated and the solid was used directly in the subsequent step. m/z 364/366 (M).

Step 7
Ethyl 3-bromo-9H-imidazo[1,5-a][1,2,4]triazolo[4,3-d][1,4]-benzodiazepine-10-carboxylate A mixture of 8-bromo-6-hydrazino-4H-2,5,10b-triaza-benzo[e]azulene-3-carboxylic acid ethyl ester (0.4 g, 0.6 mmol) in ethanol (16 mL) containing triethyl orthoformate (285 μL, 1.7 mmol) was heated under reflux for 18 h. After cooling the mixture was evaporated. Chromatography on silica gel eluting with EtOAc. Yield: 4.6 mg (5%). m/z 374/376 (M). mp 198–200° C.

EXAMPLE 4 (Method B)

6-Chloro-8-bromo-4H-2,5-10b-triaza-benzo[e]azulene-3-carboxylic Acid Ethyl Ester 8-Bromo-6-oxo-5,6-dihydro-4H-2,5,10b-triaza-benzo[e]azulene-3-carboxylic acid ethyl ester (2.3 g, 6.4 mmol) and N,N-dimethyl-p-toluidine (2.8 mL, 19.3 mmol) were mixed in chlorobenzene (25 mL) under argon. Phosphorus oxychloride (882 μL, 0.96 mmol) was added at room temperature and the resulting mixture heated under reflux for 2 h. After cooling, the mixture was evaporated. Chromatography on silica gel eluting with EtOAc. Yield: 1.4 g (59%). m/z 368/370 (M).

EXAMPLE 5

10-(3-Cyclopropyl-1,2,4-oxadiazol-5-yl)-3-methoxy-9H-imidazo[1,5-a][1,2,4]triazolo[4,3-d][1,4]benzodiazepine Step 1
3-(3-Cyclopropyl-[1,2,4]oxadiazol-5-yl)-5-(2,4-dimethoxy-benzyl)-8-methoxy-4,5-dihydro-2,5,10b-triaza-benzo[e]azulen-6-one Hexamethyldisilazane (29 mL, 139 mmol) was dissolved in TMF (250 mL), cooled to −70° C., and treated slowly with a 1.6 M solution of n-BuLi in hexane (88 mL). After stirring for 15 min. at −70° C., a solution of (E/Z)-N'-(3-cyclopropyl-[1,2,4]oxadiazol-5-ylmethyl)-N,N-dimethyl-formamidine (16.4 g, 840 mmol) in THF (50 mL) was added over 15 min. The resulting orange solution was stirred for 30 min. at −70° C., then the crude toluene solution of the 2-chloro-4-(2,4-dimethoxy-benzyl)-7-methoxy-3,4-dihydro-benzo[e][1,4]diazepin-5-one (13.5 g, 42 mmol) was added over 15 min. and stirring at −70° C. continued for 30 min. The reaction mixture was quenched at −70° C. with acetic acid (30 mL) and allowed to warm up to rt. Water (30 mL) was added and the deep red solution was heated at reflux for 2 h, and then evaporated. The residue was dissolved in $CH_2Cl_2$ (200 mL) and extracted with 1 N HCl and 10% $NaHCO_3$. The product crystallized directly from $CH_2Cl_2$ upon concentration. Yield: 11 g (53%). mp>240° C. m/z 487 (M).

Step 2
3-(3-Cyclopropyl-[1,2,4]oxadiazol-5-yl)-8-methoxy-4,5-dihydro-2,5,10b-triaza-benzo[e]azulen-6-one 3-(3-Cyclopropyl-[1,2,4]oxadiazol-5-yl)-5-(2,4-dimethoxy-benzyl)-8-methoxy-4,5-dihydro-2,5,10b-triaza-benzo[e]azulen-6-one (5 g, 10.3 mmol) were dissolved in $CH_2Cl_2$ (30 mL), cooled to 0° C., then TFA (30 mL) was added, followed by trifluoromethanesulfonic acid (2 mL, 22.9 mmol). The mixture was stirred for 4 h at rt, evaporated, the residue dissolved in $CH_2Cl_2$ (100 mL), and extracted with 10% $NaHCO_3$. The product precipitated upon evaporation of $CH_2Cl_2$. Yield: 3 g (86%); mp 245° C. m/z 337 (M).

Step 3
[3-(3-Cyclopropyl-[1,2,4]oxadiazol-5-yl)-8-methoxy-4H-2,5,10b-triaza-benzo[e]azulen-6-yl]-hydrazine 3-(3-Cyclopropyl-[1,2,4]oxadiazol-5-yl)-8-methoxy-4,5-dihydro-2,5,10b-triaza-benzo[e]azulen-6-one (1 g, 3 mmol) and N,N-dimethyl-p-toluidine (0.856 mL, 5.9 mmol) were mixed in toluene (25 mL), treated with phosphoryl bromide (0.935 g, 3.3 mmol), and refluxed for 15 h. Toluene was evaporated and the residue extracted with $CH_2Cl_2$ (50 mL) and water (50 mL). The organic layer was dried, evaporated, redissolved in THF (50 mL), and treated with a 1 M solution of anhydrous hydrazine in TBF (10 mL, 10 mmol) at reflux overnight. The mixture was evaporated and directly chromatographed on silica gel in $CH_2Cl_2$/MeOH 10:1. One obtained a light brow solid (0.4 g, 38%). m/z 352 ($MH^+$).

Step 4
10-(3-Cyclopropyl-1,2,4-oxadiazol-5-yl)-3-methoxy-9H-imidazo[1,5-a][1,2,4]triazolo[4,3-d][1,4]benzodiazepine

[3-(3-Cyclopropyl-[1,2,4]oxadiazol-5-yl)-8-methoxy-4H-2,5,10b-triaza-benzo[e]azulen-6-yl]-hydrazine (0.1 g, 2.8 mmol) and triethyl orthoformate (0.142 mL, 0.85 mmol) were refluxed in ethanol (8 mL) for 14 h. The resulting solution was cooled in ice and the white crystals filtered off. Yield: 80 mg (78%). mp 252° C. m/z 361 (M).

EXAMPLE 6

10-(3-Cyclopropyl-1,2,4-oxadiazol-5-yl)-3-methyl-9H-imidazo[1,5-a][1,2,4]triazolo[4,3-d][1,4]benzodiazepine Step 1
3-(3-Cyclopropyl-[1,2,4]oxadiazol-5-yl)-5-(2,4-dimethoxy-benzyl)-8-methyl-4,5-dihydro-2,5,10b-triaza-benzo[e]azulene-6-one 4-(2,4-Dimethoxy-benzyl)-7-methyl-3,4-dihydro-1H-benzo[e][1,4]diazepine-2,5-dione (5.0 g, 14.7 mmol) and N,N-dimethyl-p-toluidine (6.4 mL, 44.0 mmol) were mixed in toluene (50 mL) and heated to 100° C. Then phosphorus oxychloride (4.0 mL, 44.0 mmol) was added dropwise and heating at 100° C. was continued for 2 h. After cooling the mixture was evaporated and dissolved in THF (2.0 mL) and used directly in the subsequent step.

Hexamethyldisilazane (10.1 mL, 48.5 mmol) was dissolved in THF (60 mL), cooled under Argon to −70° C., and treated slowly with a 1.6 M solution of n-BuLi in hexane (30.3 mL, 48.5 mmol). After stirring for 1 h at −70° C., a solution of (E/Z)-N'-(3-cyclopropyl-[1,2,4]oxadiazol-5-ylmethyl)-N,N-dimethyl-formamidine (5.7 g, 29.4 mmol) in THF (2 mL) was added, and stirring continued for 1 h at −70° C. Then a solution of 2-chloro-4-(2,4-dimethoxy-benzyl)-7-methyl-3,4-dihydro-benzo[e][1,4]diazepine-5-one (5.28 g, 14.7 mmol) (prepared as described above) was added at −70° C., and subsequently allowed to warm up to 10° C. over 1 h, then cooled again to −30° C. After 30 min, acetic acid (17 mL) was added at −30° C. and the suspension was allowed to warm up to room temperature and water (17 mL) added and the resulting mixture stirred at room temperature for 12 h. The mixture was evaporated and then redissolved in EtOAc (100 mL). This solution was then washed with HCl (1 M, 2×50 mL) and sodium hydrogen carbonate (sat., 10 ml), dried (Na$_2$SO$_4$) and evaporated. Filtration on silica gel eluting with EtOAc: Hexane (9:1). Yield: 4.8 g (69%). m/z 471 (M).

Step 2
3(-3-Cyclopropyl-[1,2,4]oxadiazol-5-yl)-8-methyl-4,5-dihydro-2,5,10b-triaza-benzo[e]azulene-6-one 3-(3-Cyclopropyl-[1,2,4]oxadiazol-5-yl)-5-(2,4-dimethoxy-benzyl)-8-methyl-4,5-dihydro-2,5,10b-triaza-benzo[e]azulene-6-one (17.5 g, 37.1 mmol) was suspended in CH$_2$Cl$_2$ (100 mL), cooled in ice, and diluted slowly with trifluoroacetic acid (85.2 mL). The resulting solution was treated at 5° C. with trifluoromethanesulfonic acid (4.9 mL, 55.7 mmol). The red solution was stirred at room temperature for 4 h. The mixture was then evaporated and dissolved in CH$_2$Cl$_2$ (100 mL), washed with sodium hydrogen carbonate (10%, 2×50 mL) and the organic layer was dried (Na$_2$SO$_4$) and evaporated. Digestion in EtOAc (100 mL) followed by the slow addition of hexane (100 mL). The solid obtained was washed twice with EtOAc: Hexane (1:1, 2×20 mL). Yield: 9.3 g (78%) m/z 321 (M).

Step 3
6-Chloro-3-(3-cyclopropyl-[1,2,4]oxadiazol-5-yl)-8-thiomethyl-4H-2,5,10b-triaza-bezo[e]azulene 3(-3-Cyclopropyl-[1,2,4]oxadiazol-5-yl)-8-methyl-4,5-dihydro-2,5,10b-triaza-benzo[e]azulene-6-one (9.3 g, 28.8 mmol) and N,N-dimethyl-p-toluidine (12.5 mL, 86.5 mmol) were mixed in chlorobenzene (100 mL) under argon. Phosphorus oxychloride (4.0 mL, 43.2 mmol) was then added at room temperature and the resulting mixture heated under reflux for 2 h. After cooling, the mixture was evaporated and then extracted with CH$_2$Cl$_2$ (100 mL) and water (50 mL). The organic layer was separated, dried (Na$_2$SO$_4$) and evaporated. Chromatography on silica gel eluting with CH$_2$Cl$_2$: Acetone (30: 1). Yield: 3.8 g (39%). m/z 340 (MH$^+$).

Step 4
10-(3-Cyclopropyl-1,2,4-oxadiazol-5-yl)-3-methyl-9H-imidazo[1,5-a][1,2,4]triazolo[4,3-d][1,4]benzodiazepine A mixture of 6-chloro-3-(3-cyclopropyl-[1,2,4]oxadiazol-5-yl)-8-thiomethyl-4H-2,5,10b-triaza-bezo[e]azulene (3.0 g, 8.8 mmol), formylhydrazine (1.1 g, 17.7 mmol) and N,N-ethyldiisopropylamine (1.5 mL, 8.8 mmol) in chlorobenzene (30 mL) was heated under reflux for 2.5 h. After cooling, the mixture was evaporated and then extracted with CH$_2$Cl$_2$ (100 mL) and water (50 mL). The organic layer was separated, dried (Na$_2$SO$_4$) and evaporated. Chromatography on silica gel eluting with CH$_2$Cl$_2$: Acetone (30:1). Yield: 2.4 g (80%). m/z 346 (MH$^+$). mp 253–256° C.

EXAMPLE 7

10-(3-Cyclopropyl-1,2,4-oxadiazol-5-yl)-3-bromo-9H-imidazo[1,5-a][1,2,4]triazolo[4,3-d][1,4]benzodiazepine Steps 1 and 2
3-(3-Cyclopropyl-[1,2,4]oxadiazol-5-yl)-5-(2,4-dimethoxy-benzyl)-8-bromo-4,5-dihydro-2,5,10b-triaza-benzo[e]azulene-6-one 4-(2,4-Dimethoxy-benzyl)-7-bromo-3,4-dihydro-1H-benzo[e][1,4]diazepine-2,5 dione (5.0 g, 12.3 mmol) and N,N-dimethyl-p-toluidine (5.3 mL, 37.0 mmol) were mixed in toluene (20 mL) and heated to 100° C. Then phosphorus oxychloride (3.4 mL, 37.0 mmol) was added dropwise and heating at 100° C. was continued for 2 h. After cooling the mixture was evaporated and dissolved in THF (20 mL) and used directly in the subsequent step.

Hexamethyldisilazane (8.5 mL, 40.7 mmol) was dissolved in THF (60 mL), cooled under Argon to −70° C., and treated slowly with a 1.6 M solution of n-BuLi in hexane (25.5 mL, 40.7 mmol). After stirring for 1 h at −70° C., a solution of (E/Z)-N'-(3-cyclopropyl-[1,2,4]oxadiazol-5-ylmethyl)-N,N-dimethyl-formamidine (4.8 g, 24.7 mmol) in THF (2 mL) was added, and stirring continued for 1 h at −70° C. Then a solution of 2-chloro-4-(2,4-dimethoxy-benzyl)-7-bromo-3,4-dihydro-benzo[e][1,4]diazepin-5-one (5.26 g, 12.4 mmol) (prepared as described above) was added at −70° C., and subsequently allowed to warm up to 10° C. over 1 h, then cooled again to −30° C. After 30 min, acetic acid (14 mL) was added at −30° C. and the suspension was allowed to warm up to room temperature and water (14 mL) added and the resulting mixture stirred at room temperature for 1.5 h. The mixture was evaporated and then redissolved in EtOAc (100 mL). This solution was then washed with HCl (1 M, 2×50 mL) and sodium hydrogen carbonate (sat., 10 ml), dried (Na$_2$SO$_4$) and evaporated. Filtration on silica gel eluting with EtOAc: Hexane (9:1). Yield: 2.0 g (31%). m/z 536/538 (M).

Step 3
3(-3-Cyclopropyl-[1,2,4]oxadiazol-5-yl)-8-bromo-4,5-dihydro-2,5,10b-triaza-benzo[e]azulene-6-one 3-(3-Cyclopropyl-[1,2,4]oxadiazol-5-yl)-5-(2,4-dimethoxy-benzyl)-8-bromo-4,5-dihydro-2,5,10b-triaza-benzo[e]azulene-6-one (1.1 g, 2.0 mmol) was suspended in CH$_2$Cl$_2$ (6 mL), cooled in ice, and diluted slowly with trifluoroacetic acid (4.7 mL). The resulting solution was treated at 5° C. with trifluoromethanesulfonic acid (266 µL, 3.0 mmol). The red solution was stirred at room temperature for 1.5 h. The mixture was then evaporated and dissolved in CH$_2$Cl$_2$ (10 mL), washed with sodium hydrogen carbonate (sat., 10 mL) and the organic layer was dried (Na$_2$SO$_4$) and evaporated. Trituration with EtOAc. Yield: 772 mg (100%). m/z 385/387 (M—H$^−$).

Step 4
6-Chloro-3-(3-cyclopropyl-[1,2,4]oxadiazol-5-yl)-8-bromo-4H-2,5,10b-triaza-benzo[e]azulene 3(-3-Cyclopropyl-[1,2,4]oxadiazol-5-yl)-8-bromo-4,5-dihydro-2,5,10b-triaza-benzo[e]azulene-6-one (1.1 g, 20.3 mmol) and N,N-dimethyl-p-toluidine (881 μL, 6.1 mmol) were mixed in chlorobenzene (8 mL) under Argon. Phosphorus oxychloride (279 μL, 3.1 mmol) was then added at room temperature and the resulting mixture heated under reflux for 2.5 h. After cooling, the mixture was evaporated and then extracted with $CH_2Cl_2$ (50 mL) and water (25 mL). The organic layer was separated, dried ($Na_2SO_4$) and evaporated. Chromatography on silica gel eluting with $CH_2Cl_2$: Acetone (30:1). Yield: 550 mg (67%). m/z 403/405 (M—H$^-$).

Step 5
10-(3-Cyclopropyl-1,2,4-oxadiazol-5-yl)-3-bromo-9H-imidazo[1,5-a][1,2,4]triazolo[4,3-d][1,4]benzodiazepine A mixture of 6-chloro-3-(3-cyclopropyl-[1,2,4]oxadiazol-5-yl)-8-bromo-4H-2,5,10b-triaza-bezo[e]azulene (150.0 mg, 0.37 mmol), formylhydrazine (245.0 mg, 0.41 mmol) and N,N-dimethyl-p-toluidine (59 μL, 0.41 mmol) in chlorobenzene (6 mL) was heated under reflux for 3 h. After cooling, the mixture was evaporated. Chromatography on silica gel eluting with $CH_2CH_2$: acetone (30:1). Yield: 94 mg (62%). m/z 410/412 (M). mp 259–261° C.

EXAMPLE 8

10-(3-Cyclopropyl-1,2,4-oxadiazol-5-yl)-3-methylsulfanyl-9H-imidazo[1,5-a][1,2,4]triazolo[4,3-d][1,4]benzodiazepine Step 1
6-Methylsulfanyl-1H-benzo[d][1,3]oxazine-2,4-dione This intermediate is known and may be prepared by methods, known in the art, for example in the following way:

A mixture of 2-amino-5-methylbenzoic acid (4.9 g, 26.7 mmol) and ethyl chloroformate (2.9 mL, 30.0 mmol) in dioxane (25 mL) was heated under reflux for 2 h. After cooling, acetyl chloride (2.3 mL) was added and heating under reflux continued for another 3 h. After cooling, the mixture was evaporated and the resulting solid digested with tert-butyl methyl ether: heptane (1:1, 20 mL) by heating under reflux for 1 h. The soild was then filtered off and washed with tert-butyl methyl ether: heptane (1:1, 10 mL). Yield 4.8 g (85%). m/z 208 (M—H$^-$).

Step 2
4-(2,4-Dimethoxy-benzyl)-7-methylsulfanyl-3,4-dihydro-1H-benzo[e][1,4]diazepine-2,5-dione A suspension of 6-methylsulfanyl-1H-benzo[d][1,3]oxazine-2,4-dione (4.8 g, 23 mmol) containing (2,4-dimethoxy-benzylamino)-acetic acid (5.6 g, 25 mmol) in p-xylene (50 mL) was heated under reflux (150° C.) for 3 h. After cooling to room temperature the precipitate was filtered off and washed with p-xylene (2×20 ml). Yield: 7.5 g (89%). m/z 373 (MH$^+$).

Step 3
2-Chloro-4-(2,4-dimethoxy-benzyl)-7-methylsulfanyl-3,4-dihydro-benzo[e][1,4]diazepin-5-one 4-(2,4-Dimethoxy-benzyl)-7-methylsulfanyl-3,4-dihydro-1H-benzo[e][1,4]diazepine-2,5-dione (630 mg, 1.7 mmol) and N,N-dimethyl-p-toluidine (489 μL, 3.4 mmol) were mixed in toluene (5 mL) and heated to 100° C. Then phosphorus oxychloride (170 μL, 1.9 mmol) was added dropwise and heating at 100° C. was continued for 1 h. The resulting dark red solution was used directly in the subsequent step.

Step 4
3-(3-Cyclopropyl-[1,2,4]oxadiazol-5-yl)-5-(2,4-dimethoxy-benzyl)-8-methylsulfanyl-4,5-dihydro-2,5,10b-triaza-benzo[e]azulen-6-one Hexamethyldisilazane (1.2 mL, 5.6 mmol) was dissolved in THF (10 mL), cooled under argon to −70° C., and treated slowly with a 1.6 M solution of n-BuLi in hexane (3.5 mL, 5.6 mmol). After stirring for 1 h at −70° C., a solution of (E/Z)-N'-(3-cyclopropyl-[1,2,4]oxadiazol-5-ylmethyl)-N,N-dimethyl-formamidine (0.66 g, 3.3 mmol) in THF (30 mL) was added, and stirring continued for 1 h at −70° C. Then a solution of 2-chloro-4-(2,4-dimethoxy-benzyl)-7-methylsulfanyl-3,4-dihydro-benzo[e][1,4]diazepin-5-one (0.67 g, 1.7 mmol) (prepared as described above) was added at −70° C., and subsequently allowed to warm up to at 10° C. over I h, then cooled again to −30° C. After 30 min, acetic acid (4 mL) was added at −30° C. and the suspension was allowed to warm up to room temperature and water (4 mL) added and the resulting mixture heated under reflux for 6 h. After cooling, the mixture was evaporated and then redissolved in $CH_2CH_2$ (20 mL). This solution was then washed with HCl (1 M, 2×30 mL) and sodium hydrogen carbonate (sat., 30 ml), dried ($Na_2SO_4$) and evaporated. Chromatography on silica gel eluting with EtOAc. Yield: 0.29 g (34%). m/z 504 (MH$^+$).

Step 5
3-(3-Cyclopropyl-[1,2,4]oxadiazol-5-yl)-8-methylsulfanyl-4,5-dihydro-2,5,10b-triaza-benzo[e]azulen-6-one 3-(3-Cyclopropyl-[1,2,4]oxadiazol-5-yl)-5-(2,4-dimethoxy-benzyl)-8-methylsulfanyl-4,5-dihydro-2,5,10b-triaza-benzo[e]azulen-6-one (280 mg, 0.6 mmol) was suspended in $CH_2Cl_2$ (5 mL), cooled in ice, and diluted slowly with trifluroacetic acid (1.3 mL). The resulting solution was treated at 5° C. with trifluoromethanesulfonic acid (74 μL, 0.8 mmol). The red solution was stirred at room temperature for 1.5 h. The mixture was then evaporated and dissolved in $CH_2Cl_2$ (10 mL), washed with sodium hydrogen carbonate (sat., 10 mL) and the organic layer was dried ($Na_2SO_4$) and evaporated. Trituration with EtOAc. Yield: 160 mg (81%). m/z 354 (MH$^+$).

Step 6 and 7
6-Bromo-3-(3-cyclopropyl-[1,2,4]oxadiazol-5-yl)-8-methylsulfanyl-4H-2,5,10b-triaza-bezo[e]azulene and [3-(3-Cyclopropyl-[1,2,4]oxadiazol-5-yl)-8-methylsulfanyl-4H-2,5,10b-triaza-benzo[e]azulen-6-yl]-hydrazine 3-(3-Cyclopropyl-[1,2,4]oxadiazol-5-yl)-8-methylsulfanyl-4,5-dihydro-2,5,10b-triaza-benzo[e]azulen-6-one (160 mg, 0.45 mmol) and N,N-dimethyl-p-toluidine (131 μL, 0.9 mmol) were mixed in toluene (5 mL), treated with phosphoryl bromide (143 mg, 0.5 mmol) and refluxed for 5 h. After cooling, the mixture was evaporated and the residue was extracted with $CH_2Cl_2$ (10 mL) and water (10 mL). The organic layer was separated, dried ($Na_2SO_4$) and then evaporated. The residue was redissolved in THF (10 mL) and treated with an anhydrous solution of hydrazine (1 M, in THF, 1.6 mL, 0.16 mmol) and the resulting mixture heated under reflux for 12 h. After cooling the mixture was evaporated and the solid used directly in the next step. m/z 368 (MH$^+$).

Step 8
10-(3-Cyclopropyl-1,2,4-oxadiazol-5-yl)-3-methylsulfanyl-9H-imidazo[1,5-a][1,2,4]triazolo[4,3-d][1,4]benzodiazepine A mixture containing [3-(3-cyclopropyl-[1,24]oxadiazol-5-yl)-8-methylsulfanyl-4H-2,5,10b-triaza-benzo[e]azulen-6-yl]-hydrazine (210 mg, 0.57 mmol) and triethyl orthoformate (285 μL, 1.7 mmol) in ethanol (8 mL) was heated under reflux for 3 h. After cooling, the mixture was evaporated. Chromatography on silica gel eluting with EtOAc. Yield: 43 mg (20%) m/z 377 (M). mp 164–166° C.

EXAMPLE 9

Ethyl 9H-imidazo[1,5-a][1,2,4]triazolo[3,4-d][1,4]benzodiazepine-10-carboxylate

The synthesis of the title compound, pale brown solid, m.p. 263–264° C., is described in Heterocycles, Vol. 39, No. 2, 1994.

EXAMPLE 10

10-(3-Cyclopropyl-1,2,4-oxadiazol-5-yl)-9H-imidazo[1,5-a][1,2,4]triazolo[4,3-d][1,4]benzodiazepine The synthesis of the title compound, pale brown solid, m.p. 298–300° C., is described in Heterocycles, Vol. 39, No. 2, 1994.

EXAMPLE 11

Ethyl 3-fluoro-9H-imidazo[1,5-a][1,2,4]triazolo[4,3-d][1,4]benzodiazepine-10-carboxylate The synthesis of the title compound, pale brown solid, m.p. 233–234° C., is described in Heterocycles, Vol. 39, No. 2, 1994.

EXAMPLE 12

10-(3-Cyclopropyl-1,2,4-oxadiazol-5-yl)-3-fluoro-9H-imidazo[1,5-a][1,2,4]triazolo[4,3-d][1,4]benzodiazepine The synthesis of the title compound, pale brown solid, m.p. 253–254° C., is described in Heterocycles, Vol. 39, No. 2, 1994.

EXAMPLE 13

Ethyl 3-chloro-9H-imidazo[1,5-a][1,2,4]triazolo[4,3-d][1,4]benzodiazepine-10-carboxylate The synthesis of the title compound, pale brown solid, m.p. 226–227° C., is described in Heterocycles, Vol. 39, No. 2, 1994.

EXAMPLE 14

3-Chloro-10-(3-cyclopropyl-1,2,4-oxadiazol-5-yl)-9H-imidazo[1,5-a][1,2,4]triazolo[4,3-d][1,4]benzodiazepine The synthesis of the title compound, pale brown solid, m.p. 298–300° C., is described in Heterocycles, Vol. 39, No. 2, 1994.

EXAMPLE 15

7-Chloromethyl-10-(3-cyclopropyl-1,2,4-oxadiazol-5-yl)-3-methoxy-9H-imidazo[1,5-a][1,2,4]triazolo[4,3-d][1,4]benzodiazepine Analoguously to example 2 (step 4) using 2-chloro-1,1,1-trimethoxyethane Yield: 53%. mp 220° C. m/z 409 (M).

EXAMPLE 16

10-(3-Cyclopropyl-1,2,4-oxadiazol-5-yl)-3-methoxy-7-methyl-9H-imidazo[1,5-a][1,2,4]triazolo[4,3-d][1,4]benzodiazepine Analoguously to example 2 (step 4) using triethyl orthoacetate Yield: 48%. mp 222° C. m/z 376 (MH$^+$).

EXAMPLE 17

10-(3-Cyclopropyl-1,2,4-oxadiazol-5-yl)-7-ethyl-3-methoxy-9H-imidazo[1,5-a][1,2,4]triazolo[4,3-d][1,4]benzodiazepine Analoguously to example 2 (step 4) using triethyl orthopropionate Yield: 47%. mp 240° C. m/z 390 (MH$^+$).

EXAMPLE 18

Ethyl 3-methoxy-7-benzyl-9H-imidazo[1,5-a][1,2,4]triazolo[4,3-d][1,4]-benzodiazepine-10-carboxylate Analoguously to example 1 (step 7) using phenylacetic acid hydrazide.

Yield: 92%. mp 198° C. m/z 415 (M).

EXAMPLE 19

Ethyl 3-methoxy-7-methyl-9H-imidazo[1,5-a][1,2,4]triazolo[4,3-d][1,4]-benzodiazepine-10-carboxylate Analoguously to example 1 (step 7) using acetylhydrazide.

Yield: 98%. mp 210° C. m/z 339 (M).

EXAMPLE 20

Ethyl 3-methoxy-7-(1H-indol-3-ylmethyl)-9H-imidazo[1,5-a][1,2,4]triazolo[4,3-d][1,4]-benzodiazepine-10-carboxylate Analoguously to example 1 (step 7) using indole-3-acetic acid hydrazide Yield: 92%. mp 198° C. m/z 415 (M).

EXAMPLE 21

Ethyl 3-methoxy-7-[(dimethylamino)methyl]-9H-imidazo[1,5-a][1,2,4]triazolo[4,3-d][1,4]-benzodiazepine-10-carboxylate Analoguously to example 1 (step 7) using dimethylaminoacethydrazide HCl.

Yield: 38%. mp 189° C. m/z 383 (MH$^+$).

EXAMPLE 22

Ethyl 7-(2-hydroxyethyl)-3-methoxy-9H-imidazo[1,5-a][1,2,4]triazolo[4,3-d][1,4]-benzodiazepine-10-carboxylate Analogously to example 1 (step 7) using 3-hydroxypropanohydrazide, m/z 370 (MH$^+$).

EXAMPLE 23

Ethyl 7-[(2R)-5-oxo-2-pyrrolidinyl]-3-methoxy-9H-imidazo[1,5-a][1,2,4]triazolo[4,3-d][1,4]-benzodiazepine-10-carboxylate Analogously to example 1 (step 7) using (S)-5-oxo-2-pyrrolidinecarboxyhydrazide, mp 160° C., m/z 408 (M).

EXAMPLE 24

Ethyl 7-(carbamoyl)-3-methoxy-9H-imidazo[1,5-a][1,2,4]triazolo[4,3-d][1,4]-benzodiazepine-10-carboxylate Analogously to example 1 (step 7) using 2-hydrazino-2-oxo-acetamide, mp 256° C., m/z 368 (M).

EXAMPLE 25

Ethyl 7-hydroxymethyl-3-methoxy-9H-imidazo[1,5-a][1,2,4]triazolo[4,3-d][1,4]-benzodiazepine-10-carboxylate Analogously to example 1 (step 7) using hydroxy-acetic acid hydrazide, mp 255° C., m/z 355 (M).

EXAMPLE 26

Ethyl 7-(3,4-dimethoxy-benzyl)-3-methoxy-9H-imidazo[1,5-a][1,2,4]triazolo[4,3-d][1,4]-benzodiazepine-10-carboxylate Analogously to example 1 (step 7) using 3,4-dimethoxyphenylacetic acid hydrazide, mp 196° C., m/z 476 (MH+).

EXAMPLE 27

Ethyl 3-methoxy-7-(3-methoxybenzyl)-9H-imidazo[1,5-a][1,2,4]triazolo[4,3-d][1,4]-benzodiazepine-10-carboxylate Analogously to example 1 (step 7) using 3-methoxyphenylacetic acid hydrazide, mp 209° C. m/z 446 (MH+).

EXAMPLE 28

Ethyl 3-chloro-7-benzyl-9H-imidazo[1,5-a][1,2,4]triazolo[4,3-d][1,4]-benzodiazepine-10-carboxylate Analogously to example 1 (step 7) using phenylacetic acid hydrazide, mp 188° C., mp z 420 MH+).

EXAMPLE 29

Ethyl-3-chloro-7-(1H-indol-3-ylmethyl)-9H-imidazol[1,5-a][1,2,4]triazolo[4,3-d][1,4]-benzodiazepine-10-carboxylate Analogously to example 1 (step 7) using indole-3-acetic acid hydrazide, mp 242° C., m/z 459 MH+).

EXAMPLE 30

Ethyl 7-(carbamoyl)-3-chloro-9H-imidazo[1,5-a][1,2,4]triazolo[4,3-d][1,4]-benzodiazepine-10-carboxylate Analogously to example 1 (step 7) using oxamic hydrazide, mp>250° C., m/z 373 (MH+).

EXAMPLE 31

Ethyl 3-methoxy-7-[(3-methyl-1H-indol-2-yl)methyl]-9H-imidazo[1,5-a][1,2,4]triazolo[4,3-d][1,4]-benzodiazepine-10-carboxylate Analguously to example 1 (step 7) using (2-methyl-1H-indol-3-yl)-acetic acid hydrazide, mp 220° C., m/z 203 (M).

EXAMPLE 32

Ethyl 3-methoxy-7-[(5-methyl-1H-indol-2-yl)methyl]-9H-imidazo[1,5-a][1,2,4]triazolo[4,3-d][1,4]-benzodiazepine-10-carboxylate Analogously to example 1 (step 7) using (5-methyl-1H-indol-3-yl)-acetic acid hydrazide, mp>250° C., m/z 468 (M).

EXAMPLE 33

Ethyl 7-(2-chloro-benzyl)-3-methoxy-9H-imidazo[1,5-a][1,2,4]triazolo[4,3-d][1,4]-benzodiazepine-10-carboxylate Analogously to example 1 (step 7) using (2-chloro-phenyl)-acetic acid hydrazide, mp 215° C., m/z 449(M).

EXAMPLE 34

Ethyl 3-methoxy-7-(2-methoxybenzyl)-9H-imidazo[1,5-a][1,2,4]triazolo[4,3-d][1,4]-benzodiazepine-10-carboxylate Analogously to example 1 (step 7) using (2-methoxy-phenyl)-acetic acid hydrazide, mp 80° C., m/z 445(M).

EXAMPLE 35

Ethyl 7-(diethylcarbamoyl)-3-methoxy-9H-imidazo[1,5-a][1,2,4]triazolo[4,3-d][1,4]-benzodiazepine-10-carboxylate Analogously to example 1 (step 7) using N,N-diethyl-2-hydrazino-2-oxo-acetamide, mp 75° C., m/z 425 (MH+).

EXAMPLE 36

Ethyl 3-methoxy-7-(2-trifluoromethyl-benzyl)-9H-imidazo[1,5-a][1,2,4]triazolo[4,3-d][1,4]-benzodiazepine-10-carboxylate Analogously to example 1 (step 7) using (2-trifluoromethyl-phenyl)-acetic acid hydrazide, mp 225° C., m/z 483 (M).

EXAMPLE 37

Ethyl 3-methoxy-7-[(7-methoxy-1H-indol-3-yl)methyl]-9H-imidazo[1,5-a][1,2,4]triazolo[4,3-d][1,4]-benzodiazepine-10-carboxylate Analogously to example 1 (step 7) using (5-methoxy-1H-indol-3-yl)-acetic acid hydrazide, mp>250° C., m/z 485 (MH+).

EXAMPLE 38

Ethyl 7-(3-benzo[1,3]dioxol-5-ylmethyl)-3-chloro-9H-imidazo[1,5-a][1,2,4]triazolo[4,3-d][1,4]-benzodiazepine-10-carboxylate Analogously to example 1 (step 7) using benzo[1,3]dioxol-5-yl-acetic acid hydrazide, m/z 463 (M).

EXAMPLE 39

Ethyl 3-methoxy-7-(4-methoxybenzyl)-9H-imidazo[1,5-a][1,2,4]triazolo[4,3-d][1,4]-benzodiazepine-10-carboxylate Analogously to example 1 (step 7) using (4-methoxy-phenyl)-acetic acid hydrazide, mp 179° C., m/z 445 (M).

EXAMPLE 40

Ethyl 3-methoxy-7-(3-trifluoromethyl-benzyl)-9H-imidazo[1,5-a][1,2,4]triazolo[4,3-d][1,4]-benzodiazepine-10-carboxylate Analogously to example 1 (step 7) using (3-trifluoromethyl-phenyl)-acetic acid hydrazide, mp 89° C., m/z 483 (M).

EXAMPLE 41

Ethyl 3-chloro-7-(4-trifluoromethyl-benzyl)-9H-imidazo[1,5-a][1,2,4]triazolo[4,3-d][1,4]-benzodiazepine-10-carboxylate Analogously to example 1 (step 7) using (4-trifluoromethyl-phenyl)-acetic acid hydrazide, mp 217° C., m/z 487 (M).

EXAMPLE 42

Ethyl 3-chloro-7-(4-dimethylamino-benzyl)-9H-imidazo[1,5-a][1,2,4]triazolo[4,3-d][1,4]-benzodiazepine-10-carboxylate Analogously to example 1 (step 7) using (4-dimethylamino-phenyl)-acetic acid hydrazide, mp 206° C., m/z 463 (M+).

EXAMPLE 43

Ethyl 3-chloro-7-(2,4-dimethoxy-benzyl)-9H-imidazo[1,5-a][1,2,4]triazolo[4,3-d][1,4]-benzodiazepine-10-carboxylate Analogously to example 1 (step 7) using (2,4-dimethoxy-phenyl)-acetic acid hydrazide, mp 160° C., m/z 479 (M).

EXAMPLE 44

Ethyl 3-chloro-7-(4-methoxy-benzyl)-9H-imidazo[1,5-a][1,2,4]triazolo[4,3-d][1,4]-benzodiazepine-10-carboxylate Analogously to example 1 (step 7) using (4-methoxy-phenyl)-acetic acid hydrazide, m/z 499 (M).

EXAMPLE 45

10-(3-Cyclopropyl-1,2,4-oxadiazol-5-yl)-7-benzyl-3-bromo-9H-imidazo[1,5-a][1,2,4]triazolo[4,3-d][1,4]benzodiazepine Analogously to example 7 (step 5) using, phenylacetic acid hydrazide, mp 233–235° C., m/z 500/502 (M).

EXAMPLE 46

10-(3-Cyclopropyl-1,2,4-oxadiazol-5-yl)-7-(1H-indol-3-ylmethyl)-3-bromo-9H-imidazo[1,5-a][2,4]triazolo[4,3-d][1,4]benzodiazepine Analogously to example 7 (step 5) using indole-3-acetic acid hydrazide, mp 265° C. (dec), m/z 539/541 (M).

EXAMPLE 47

Ethyl 3-bromo-7-(1H-indol-3-ylmethyl)-9H-imidazo[1,5-a][1,2,4]triazolo[4,3-d][1,4]-benzodiazepine-10-carboxylate Analogously to example 4 (Method B) using indole-3-acetic acid hydrazide, mp 258° C. (dec), m/z 503/505 (M).

EXAMPLE 48

Ethyl 3-bromo-7-benzyl-9H-imidazo[1,5-a][1,2,4]triazolo[4,3-d][1,4]-benzodiazepine-10-carboxylate Analogously to example 4 (Method B) using indole-3-acetic acid hydrazide, mp 190–192° C. (dec), m/z 464/466 (M).

EXAMPLE 49

Ethyl 7-(benzo[1,3]dioxol-5-yl)-3-methoxy-9H-imidazo[1,5-a][1,2,4]triazolo[4,3-d][1,4]-benzodiazepine-10-carboxylate Analogously to example 1 (step 7) using 3,4-methylenedioxy-benzhydrazide, mp 247° C., m/z 446 (MH+).

EXAMPLE 50

Ethyl 3-bromo-7-(3-methoxy-benzyl)-9H-imidazo[1,5-a][1,2,4]triazolo[4,3-d][1,4]-benzodiazepine-10-carboxylate Analogously to example 4 (Method B) using 3-methoxyphenylacetic acid hydrazide, mp 111–113° C., m/z 494/496 (M).

EXAMPLE 51

Ethyl 3-bromo-7-(3,4-dimethoxy-benzyl)-9H-imidazo[1,5-a][1,2,4]triazolo[4,3-d][1,4]-benzodiazepine-10-carboxylate Analogously to example 4 (Method B) using 3,4-dimethoxyphenylacetic acid hydrazide, mp 224–226° C., m/z 524/526 (M).

EXAMPLE 52

Ethyl 7-[2-benzo[1,3]dioxol-5-yl)-ethyl]-3-chloro-9H-imidazo[1,5-a][1,2,4]triazolo[4,3-d][1,4]-benzodiazepine-10-carboxylate Analogously to example 4 (Method B) 3-(3,4-methylenedioxyphenyl)propionic acid hydrazide, mp 208° C., m/z 476.9 (M).

EXAMPLE 53

Ethyl 7-(4-methanesulfonyl-benzyl)-3-methoxy-9H-imidazo[1,5-a][1,2,4]triazolo[4,3-d][1,4]-benzodiazepine-10-carboxylate Analogously to example 4 (Method B) using 4-methanesulfonyl-phenylacetic acid hydrazide, white foam, m/z 494(MH+).

EXAMPLE 54

Ethyl 3-methoxy-7-[(biphenyl-4-yl)methyl]-9H-imidazo[1,5-a][1,2,4]triazolo[4,3-d][1,4]-benzodiazepine-10-carboxylate Analogously to example 4 (Method B) using 4-biphenylacetic acid hydrazide, white foam, m/z 492 (MH+).

EXAMPLE 55

Ethyl 7-(4-dimethylamino-benzyl)-3-methoxy-9H-imidazo[1,5-a][1,2,4]triazolo[4,3-d][1,4]-benzodiazepine-10-carboxylate Analogously to example 4 (Method B) using 4-dimethylaminophenylacetic acid hydrazide, mp 210° C., m/z 459(MH+).

EXAMPLE 56

Ethyl 3-methoxy-7-(4-trifluoromethoxy-benzyl)-9H-imidazo[1,5-a][1,2,4]triazolo[4,3-d][1,4]-benzodiazepine-10-carboxylate Analogously to example 4 (Method B) using 4-trifluoromethoxy-phenylacetic acid hydrazide, mp 225° C., m/z 500(MH+).

EXAMPLE 57

Ethyl 3-chloro-7-(4-nitro-benzyl)-9H-imidazo[1,5-a][1,2,4]triazolo[4,3-d][1,4]-benzodiazepine-10-carboxylate Analogously to example 4 (Method B) using 4-nitrophenylacetic acid hydrazide, white foam, m/z 462(M).

EXAMPLE 58

10-(3-Cyclopropyl-1,2,4-oxadiazol-5-yl)-7-(4-dimethylamino-benzyl)-3-bromo-9H-imidazo[1,5-a][1,2,4]triazolo[4,3-d][1,4]benzodiazepine Analogously to example 7 (step 5) using 4-dimethylaminophenylacetic acid hydrazide, mp 140° C. (dec), m/z 543/545 (M).

EXAMPLE 59

Ethyl 3-bromo-7-(4-dimethylamino-benzyl)-9H-imidazo[1,5-a][1,2,4]triazolo[4,3-d][1,4]-benzodiazepine-10-carboxylate Analogously to example 4 (Method B) using 4-dimethylaminophenylacetic acid hydrazide, mp 240° C. (dec.), m/z 507/509 (M).

EXAMPLE 60

3-Chloro-10-(5-cyclopropyl-1,2,4-oxadiazol-3-yl)-9H-imidazo[1,5-a][1,2,4]triazolo[4,3-d][1,4]benzodiazepine Step 1
8-Chloro-5-(2,4-dimethoxy-benzyl)-6-oxo-5,6-dihydro-4H-2,5,10b-triaza-benzo[e]azulene-3-carboxylic Acid Amide Ethyl 3-chloro-9H-imidazo[1,5-a][1,2,4]triazolo[4,3-d][1,4]benzodiazepine-10-carboxylate (Example 13) (7.1 g, 15.7 mmol) was suspended in dioxane (60 mL). Formamide (2.8 mL, 71.3 mmol) was added. A 5.4 M solution of sodium methylate in methanol (2.9 mL, 15.5 mmol) was added slowly and the mixture was stirred overnight at rt. The resulting white suspension was diluted with water (70 mL) and stirred for 1 h at rt. Dioxane was removed under reduced pressure, the suspension was stirred for 1 h in ice, the crystals were filtered off, washed with water, and dried at 60° C./0.1 mbar. One obtained white crystals (6 g, 89%). mp>220° C. m/z 427 (MH+)

Step 2
8-Chloro-5-(2,4-dimethoxy-benzyl)-6-oxo-5,6-dihydro-4H-2,5,10b-triaza-benzo[e]azulene-3-carbonitrile 8-Chloro-5-(2,4-dimethoxy-benzyl)-6-oxo-5,6-dihydro-4H-2,5,10b-triaza-benzo[e]azulene-3-carboxylic acid amide (5.9 g, 13.8 mmol) and phosphorous oxychloride (1.4 mL, 15.2 mmol) were mixed in dioxane (55 mL) and refluxed overnight. The resulting yellow solution was evaporated and the residue purified by chromatography on silica gel in $CH_2Cl_2$/acetone 20:1. One obtained a white foam (3.5 g, 61%). m/z 408 (MH+)

Step 3
8-Chloro-5-(2,4-dimethoxy-benzyl)-N-hydroxy-6-oxo-5,6-dihydro-4H-2,5,10b-triaza-benzo[e]azulene-3-carboxamidine 8-Chloro-5-(2,4-dimethoxy-benzyl)-6-oxo-5,6-dihydro-4H-2,5,10b-triaza-benzo[e]azulene-3-carbonitrile (2 g, 4.9 mmol) and hydroxylamine HCl (1 g, 14.6 mmol) were suspended in DMF (10 mL) and treated slowly with a 5.4 M solution of sodium methylate in methanol (2.7 mL, 14.6 mmol). The yellow suspension was stirred overnight. The suspension was cooled in ice and diluted with water (20 mL) and stirred for 1 h in ice. The crystals were filtered off and washed with cold water (5 mL). One obtained white crystals (1.9 g, 89%). m/z 442 (MH+).

Step 4
8-Chloro-3-(5-cyclopropyl-[1,2,4]oxadiazol-3-yl)-5-(2,4-dimethoxy-benzyl)-4,5-dihydro-2,5,10b-triaza-benzo[e]azulen-6-one 8-Chloro-5-(2,4-dimethoxy-benzyl)-N-hydroxy-6-oxo-5,6-dihydro-4H-2,5,10b-triaza-benzo[e]azulene-3-carboxamidine (1.9 g, 4.3 mmol), magnesiumoxide (0.156 g, 3.9 mmol), and cyclopropanecarbonyl chloride (0.5 mL, 5.3 mmol) were refluxed in dioxane overnight. Dioxane was evaporated and the residue dissolved in DMF (20 mL) and refluxed for 1 h. DMF was evaporated and the residue extracted with $CH_2Cl_2$ and water. The product crystallized upon concentration of the organic layer and dilution with ethyl acetate. One obtained a white solid (0.8 g, 39%). mp 198–205° C. m/z 492 (MH+).

Step 5
8-Chloro-3-(5-cyclopropyl-[1,2,4]oxadiazol-3-yl)-4,5-dihydro-2,5,10b-triaza-benzo[e]azulen-6-one 8-Chloro-3-(5-cyclopropyl-[1,2,4]oxadiazol-3-yl)-5-(2,4-dimethoxy-benzyl)-4,5-dihydro-2,5,10b-triaza-benzo[e]azulen-6-one (2 g, 4 mmol) was dissolved in $CH_2Cl_2$ (8 mL) and trifluoroacetic acid (8 mL), cooled in ice and treated slowly with trifluorometanesulfonic acid (0.7 mL, 8 mmol) and then stirred for 2 h without cooling. The solvents were evaporated and the residue extracted with $CH_2Cl_2$ and water. From the organic layer one obtained a white foam (0.84 g, 62%). m/z 342(MH+).

Step 6
6,8-Dichloro-3-(5-cyclopropyl-[1,2,4]oxadiazol-3-yl)-4H-2,5,10b-triaza-benzo[e]azulene 8-Chloro-3-(5-cyclopropyl-[1,2,4]oxadiazol-3-yl)-4,5-dihydro-2,5,10b-triaza-benzo[e]azulen-6-one (0.84 g, 2.5 mmol) was suspended in chlorobenzene (8 mL), N,N-dimethyl-p-toluidine (1.1 mL, 7.4 mmol) and phosphorus oxychloride (0.34 mL, 3.7 mmol) were added and the mixture was refluxed overnight. The resulting solution was evaporated and the residue was purified by chromatography on silica gel in $CH_2Cl_2$/acetone 10:1. One obtained a white solid (0.56 g, 63%). mp 200° C. m/z 359(M).

Step 7
3-Chloro-10-(5-cyclopropyl-1,2,4-oxadiazol-3-yl)-9H-imidazo[1,5-a][1,2,4]triazolo[4,3-d][1,4]benzodiazepine 6,8-Dichloro-3-(5-cyclopropyl-[1,2,4]oxadiazol-3-yl)-4H-2,5,10b-triaza-benzo[e]azulene (70 mg, 0.194 mmol), formylhydrazine (23 mg, 0.39 mmol) and N-ethyldiisopropylamine (0.066 mL, 0.39 mmol) were mixed in chlorobenzene and refluxed for 3.5 h. The solvent was evaporated, the residue extracted with $CH_2Cl_2$/water and then purified by chromatography on silica gel in $CH_2Cl_2$/2-propanol 20:1. One obtained a white solid (36 mg, 50%). mp>230° C. m/z 365(M).

EXAMPLE 61

3-Chloro-10-(5-cyclopropyl-1,2,4-oxadiazol-3-yl)-7-(1H-indol-3-ylmethyl)-9H-imidazo[1,5-a][1,2,4]triazolo[4,3-d][1,4]benzodiazepine Analogously to example 60 using indole-3-acetic acid hydrazide, white foam, m/z 499(MH+).

EXAMPLE 62

3-Chloro-10-(5-cyclopropyl-1,2,4-oxadiazol-3-yl)-7-(4-dimethylamino-benzyl)-9H-imidazo[1,5-a][1,2,4]triazolo[4,3-d][1,4]benzodiazepine Analogously to example 60 using using (4-dimethylamino-phenyl)-acetic acid hydrazide, white solid, m/z 495(MH+)

EXAMPLE 63

7-Benzyl-3-chloro-10-(5-cyclopropyl-1,2,4-oxadiazol-3-yl)-9H-imidazo[1,5-a][1,2,4]triazolo[4,3-d][1,4]benzodiazepine Analogously to example 60 using phenylacetic acid hydrazide, white solid, m/z 456(MH+)

EXAMPLE 64

3-Chloro-7-cyclopropylmethyl-10-(5-cyclopropyl-1,2,4-oxadiazol-3-yl)-9H-imidazo[1,5-a][1,2,4]triazolo[4,3-d][1,4]benzodiazepine Analogously to example 60 using cyclopropyl-acetic acid hydrazide, white solid, m/z 420 (M)

EXAMPLE 65

3-Chloro-10-(5-cyclopropyl-1,2,4-oxadiazol-3-yl)-7-(3,4-dimethoxy-benzyl)-9H-imidazo[1,5-a][1,2,4]triazolo[4,3-d][1,4]benzodiazepine Analogously to example 60 using 3,4-dimethoxy-phenylacetic acid hydrazide, colorless gum, m/z 515 (M).

EXAMPLE 66

3-Chloro-10-(5-cyclopropyl-1,2,4-oxadiazol-3-yl)-7-(5-methyl-1H-indol-3-ylmethyl)-9H-imidazo[1,5-a][1,2,4]triazolo[4,3-d][1,4]benzodiazepine Analogously to example 60 using (5-methyl-1H-indol-3-yl)-acetic acid hydrazide, brown solid, m/z 509 (M).

EXAMPLE 67

3-Chloro-10-(5-cyclopropyl-1,2,4-oxadiazol-3-yl)-7-(3-methoxy-benzyl)-9H-imidazo[1,5-a][1,2,4]triazolo[4,3-d][1,4]benzodiazepine Analogously to example 60 using 3-methoxy-phenylacetic acid hydrazide, white foam, m/z 485 (M).

EXAMPLE 68

Ethyl 3-hydroxy-9H-imidazo[1,5-a][1,2,4]triazolo[4,3-d][1,4]-benzodiazepine-10-carboxylate Step 1
6-Hydroxy-1H-benzo[d][1,3]oxazine-2,4-dione 5-Hydroxyanthranilic acid (9.5 g, 62 mmol) was suspended in dioxane (50 mL), bis(trichloromethyl)carbonate (6 g, 20 mmol) was added (slightly exothermic), the suspension was refluxed for 1 h, allowed to cool to rt, the solid was filtered off and washed with dioxane, affording brown crystals (10.1 g, 90%), mp. 236° C. (dec).

Step 2
6-(tert-Butyl-diphenyl-silanyloxy)-1H-benzo[d][1,3]oxazine-2,4-dione

6-Hydroxy-1H-benzo[d][1,3]oxazine-2,4-dione (9.7 g, 54 mmol), tert-butyldiphenylchlorosilane (15.2 mL, 59 mmol) and imidazole (4 g, 59 mmol) were stirred in DMF (100 mL) for 24 h at rt. The reaction mixture was extracted with ethyl acetate (400 mL) and water 300 mL). The product in the organic layer was purified by chromatography on silica gel in hexane/ethyl acetate 2:1 and then crystallized from hot ethyl acetate/hexane, affording white crystals (13 g, 58%), mp. 185° C.

Step 3
7-(tert-Butyl-diphenyl-silanyloxy)-4-(2,4-dimethoxy-benzyl)-3,4-dihydro-1H-benzo[e][1,4]diazepine-2,5-dione Analogously to example 1 (step 2), the crude product was purified by chromatography on silica gel in hexane/ethyl acetate 1:1, affording a white foam in 80% yield. 580 (M).

Step 4
8-(tert-Butyl-diphenyl-silanyloxy)-5-(2,4-dimethoxy-benzyl)-6-oxo-5,6-dihydro-4H-2,5,10b-triaza-benzo[e]azulene-3-carboxylic Acid Ethyl Ester Analogously to example 1 (step 3 and 4), the crude product was purified by chromatography on silica gel in hexane/ethyl acetate 1:2, affording a yellow foam in 54% yield. 675 (M).

Step 5
8-(tert-Butyl-diphenyl-silanyloxy)-6-oxo-5,6-dihydro-4H-2,5,10b-triaza-benzo[e]azulene-3-carboxylic Acid Ethyl Ester Analogously to example 1 (step 5), limiting the reaction time to 1 h, the crude product was purified by chromatography on silica gel in dichloromethane/2-propanol 30:1, affording a white foam in 65% yield. 526 (MH+).

Step 6
8-(tert-Butyl-diphenyl-silanyloxy)-6-chloro-4H-2,5,10b-triaza-benzo[e]azulene-3-carboxylic Acid Ethyl Ester Analogously to example 1 (step 6), the crude product was purified by chromatography on silica gel in hexane/ethyl acetate 1:1, affording a white foam in 10% yield. 543 (M).

Step 7
Ethyl 3-(tert-butyl-diphenyl-silanyloxy)-9H-imidazo[1,5-a][1,2,4]triazolo[4,3-d][1,4]-benzodiazepine-10-carboxylate Analogously to example 1 (step 7), the crude product was purified by chromatography on silica gel in ethyl acetate, affording white crystals in 46% yield, mp 233° C.

Step 8
Ethyl 3-hydroxy-9H-imidazo[1,5-a][1,2,4]triazolo[4,3-d][1,4]-benzodiazepine-10-carboxylate Ethyl 3-(tert-butyl-diphenyl-silanyloxy)-9H-imidazo[1,5-a][1,2,4]triazolo[4,3-d][1,4]-benzodiazepine-10-carboxylate (155 mg, 0.28 mmol) was stirred in an 1 M solution of tetrabutylammonium fluoride (1 mL) for 30 min. The mixture was extracted with dichloromethane and water. The crude product was purified by chromatography on silica gel in DCM/MeOH 40:3. One obtained white crystals (55 mg, 62%), mp>250° C., 310 (M—H)$^-$.

EXAMPLE 69

Ethyl 3-chloro-7-(pyridin-4-ylmethyl)-9H-imidazo[1,5-a][1,2,4]triazolo[4,3-d][1,4]-benzodiazepine-10-carboxylate Analogously to example 4 (Method B) using 4-pyridine-acetic acid hydrazide dihydrochloride, light brown solid, mp 213° C., m/z 421(MH+).

References ([1]) Hunkeler, W.; Kyburz, E;. EP 150040
([2]) Rogers-Evans, M.; Spurr, P.; EP 787729
([3]) Zhang, P.; Zhang, W.; Liu, R.; Harris, B.; Skolnick, P.; Cook, J. M. J. Med. Chem. 1995, 38, 1679–88.
([4]) Gerecke, M.; Kyburz, E.; Borer, R.; Gassner, W.; Heterocycles, 1994, 39, 693–721.

EXAMPLE A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

| | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

| | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository molds of suitable size, left to cool, the suppositories are then removed from the molds and packed individually in wax paper or metal foil.

What is claimed is:

1. A compound of the formula

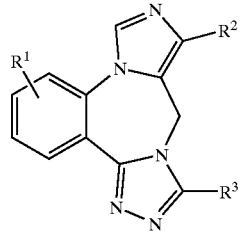

I wherein
$R^1$ is hydrogen, halogen, lower alkyl, lower alkoxy, hydroxy, cyano, trifluoromethyl, trifluoromethoxy or lower alkylthio;
$R^2$ is —C(O)O-lower alkyl, unsubstituted isoxazolyl, 1,2,4-oxadiazol-3-yl or 1,2,4-oxadiazol-5-yl, or isoxazolyl, 1,2,4-oxadiazol-3-yl or 1,2,4-oxadiazol-5-yl substituted by lower alkyl, trifluoromethyl or cycloalkyl;
$R^3$ is hydrogen, lower alkyl, —$(CH_2)_n$-cycloalkyl, —$(CH_2)_n$-halogen, —$(CH_2)_n$-pyridin-4-yl, or unsubstituted —$(CH_2)_n$-phenyl, or —$(CH_2)_n$-phenyl substituted by one or two substituents selected from the group consisting of lower alkoxy, halogen, —$SO_2CH_3$, phenyl, $OCF_3$, nitro, $CF_3$, —$NR_2$, or is unsubstituted —$(CH_2)_n$-indolyl, or —$(CH_2)_n$-indolyl substituted by lower alkyl or lower alkoxy, or is pyrrolidinyl-5-oxo, —C(O)—$NR_2$, —$(CH_2)_n$-OH, —$(CH_2)_n$-$NR_2$ or —$(CH_2)_n$-benzo [1,3]dioxole;
R is hydrogen or lower alkyl; and
n is 0, 1, 2 or 3;
or a pharmaceutically acceptable acid addition salt thereof, with the exception of the following compounds:
ethyl 9H-imidazo[1,5-a][1,2,4]triazolo[3,4-d][1,4]benzodiazepine-10-carboxylate, 10-(3-cyclopropyl-1,2,4-oxadiazol-5-yl)-9H-imidazo[1,5-a][1,2,4]triazolo[4,3-d][1,4]benzodiazepine,
ethyl 3-fluoro-9H-imidazo[1,5-a][1,2,4]triazolo[4,3-d][1,4]benzodiazepine-10-carboxylate, 10-(3-cyclopropyl-1,2,4-oxadiazol-5-yl)-3-fluoro-9H-imidazo[1,5-a][1,2,4]triazolo[4,3-d][1,4]benzodiazepine,
ethyl 3-chloro-9H-imidazo[1,5-a][1,2,4]triazolo[4,3-d][1,4]benzodiazepine-10-carboxylate and 3-chloro-10-(3-cyclopropyl-1,2,4-oxadiazol-5-yl)-9H-imidazo[1,5-a][1,2,4]triazolo[4,3-d][1,4]benzodiazepine.

2. A compound of the formula

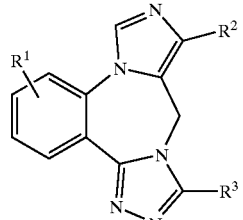

I wherein
$R^1$ is hydrogen, halogen, lower alkyl, lower alkoxy, cyano, trifluoromethyl, trifluoromethoxy or lower alkylthio;

R² is —C(O)O-lower alkyl, unsubstituted isoxazolyl, 1,2,4-oxadiazol-3-yl or 1,2,4-oxadiazol-5-yl, or isoxazolyl, 1,2,4-oxadiazol-3-yl or 1,2,4-oxadiazol-5-yl, substituted by lower alkyl, trifluoromethyl or cycloalkyl;

R³ is hydrogen, lower alkyl, —(CH₂)ₙ-halogen, unsubstituted —(CH₂)ₙ-phenyl, or —(CH₂)ₙ-phenyl substituted by one or two substituents selected from lower alkoxy, halogen, CF₃, —NR₂, or is unsubstituted-(CH₂)ₙ-indolyl, or —(CH₂)ₙ-indolyl substituted by lower alkyl or lower alkoxy, or is pyrrolidinyl-5-oxo, —C(O)—NR₂, —(CH₂)ₙ—OH, —(CH₂)ₙ—NR₂ or benzo[1,3]dioxole;

R is hydrogen or lower alkyl; and n is independently from each other 0, 1, 2 or 3;

or a pharmaceutically acceptable acid addition salt thereof, with the exception of the following compounds:

ethyl 9H-imidazo[1,5-a][1,2,4]triazolo[3,4-d][1,4] benzodiazepine-10-carboxylate, 10-(3-cyclopropyl-1,2,4-oxadiazol-5-yl)-9H-imidazo[1,5-a][1,2,4]triazolo[4,3-d][1,4]benzodiazepine, ethyl 3-fluoro-9H-imidazo[1,5-a][1,2,4]triazolo[4,3-d][1,4]benzodiazepine-10-carboxylate, 10-(3-cyclopropyl-1,2,4-oxadiazol-5-yl)-3-fluoro-9H-imidazo[1,5-a][1,2,4]triazolo[4,3-d][1,4]benzodiazepine, ethyl 3-chloro-9H-imidazo[1,5-a][1,2,4]triazolo[4,3-d][1,4]benzodiazepine-10-carboxylate and 3-chloro-10-(3-cyclopropyl-1,2,4-oxadiazol-5-yl)-9H-imidazo[1,5-a][1,2,4]triazolo[4,3-d][1,4]benzodiazepine.

3. A compound of formula I according to claim 1, wherein R² is —C(O)O-lower alkyl.

4. A compound of formula I according to claim 3, wherein R³ is hydrogen and R¹ is hydrogen, methoxy, methyl, —SCH₃ or halogen.

5. A compound of formula I according to claim 4, which is ethyl 3-methoxy-9H-imidazo[1,5-a][1,2,4]triazolo[4,3-d][1,4]-benzodiazepine-10-carboxylate.

6. A compound of formula I according to claim 4, which is ethyl 3-methyl-9H-imidazo[1,5-a][1,2,4]triazolo[3,4-d][1,4]benzodiazepine-10-carboxylate.

7. A compound of formula I according to claim 4, which is ethyl 3-bromo-9H-imidazo[1,5-a][1,2,4]triazolo[4,3-d][1,4]-benzodiazepine-10-carboxylate.

8. A compound of formula I according to claim 3, wherein R³ is —CH₂OH, —(CH₂)₂-methylenedioxyphenyl, methyl, unsubstituted —CH₂-indolyl, or —CH₂-indolyl substituted by methoxy, or is CH₂-phenyl substituted by —SO₂CH₃, phenyl, —OCF₃, —N(CH₃)₂, NO₂ or methoxy, and R¹ is methoxy, chloro or bromo.

9. A compound of formula I according to claim 8, which is ethyl 3-methoxy-7-methyl-9H-imidazo[1,5-a][1,2,4]triazolo[4,3-d][1,4]-benzodiazepine-10-carboxylate, ethyl 3-methoxy-7-(1H-indol-3-ylmethyl)-9H-imidazo[1,5-a][1,2,4]triazolo[4,3-d][1,4]-benzodiazepine-10-carboxylate, ethyl 7-hydroxymethyl-3-methoxy-9H-imidazo[1,5-a][1,2,4]triazolo[4,3-d][1,4]-benzodiazepine-10-carboxylate, ethyl 3-methoxy-7-(3-methoxybenzyl)-9H-imidazo[1,5-a][1,2,4]triazolo[4,3-d][1,4]-benzodiazepine-10-carboxylate, ethyl 3-methoxy-7-[(7-methoxy-1H-indol-3-yl)methyl]-9H-imidazo[1,5-a][1,2,4]triazolo[4,3-d][1,4]-benzodiazepine-10-carboxylate, ethyl-3-bromo-7-(1H-indol-3-ylmethyl)-9H-imidazo[1,5-a][1,2,4]triazolo[4,3-d][1,4]-benzodiazepine-10-carboxylate, ethyl-3-bromo-7-(3-methoxy-benzyl)-9H-imidazo[1,5-a][1,2,4]triazolo[4,3-d][1,4]-benzodiazepine-10-carboxylate, ethyl 7-[2-benzo[1,3]dioxol-5-yl)-ethyl]-3-chloro-9H-imidazo[1,5-a][1,2,4]triazolo[4,3-d][1,4]-benzodiazepine-10-carboxylate, ethyl 7-(4-methanesulfonyl-benzyl)-3-methoxy-9H-imidazo[1,5-a][1,2,4]triazolo[4,3-d][1,4]-benzodiazepine-10-carboxylate, ethyl 3-methoxy-7-[(biphenyl-4-yl)methyl]-9H-imidazo[1,5-a][1,2,4]triazolo[4,3-d][1,4]-benzodiazepine-10-carboxylate, ethyl 3-methoxy-7-(4-trifluoromethoxy-benzyl)-9H-imidazo[1,5-a][1,2,4]triazolo[4,3-d][1,4]-benzodiazepine-10-carboxylate, ethyl 3-chloro-7-(4-nitro-benzyl)-9H-imidazo[1,5-a][1,2,4]triazolo[4,3-d][1,4]-benzodiazepine-10-carboxylate, ethyl 7-(4-dimethylamino-benzyl)-3-methoxy-9H-imidazo[1,5-a][1,2,4]triazolo[4,3-d][1,4]-benzodiazepine-10-carboxylate, ethyl 3-bromo-7-(1H-indol-3-ylmethyl)-9H-imidazo[1,5-a][1,2,4]triazolo[4,3-d][1,4]-benzodiazepine-10-carboxylate ethyl 3-bromo-7-(3-methoxy-benzyl)-9H-imidazo[1,5-a][1,2,4]triazolo[4,3-d][1,4]-benzodiazepine-10-carboxylate or ethyl 3-bromo-7-(4-dimethylamino-benzyl)-9H-imidazo[1,5-a][1,2,4]triazolo[4,3-d][1,4]-benzodiazepine-10-carboxylate.

10. A compound of formula I according to claim 1, wherein R² is the group 3-cyclopropyl-[1,2,4]oxadiazol-5-yl.

11. A compound of formula I according to claim 10, wherein R³ is hydrogen and R¹ is hydrogen, methoxy, methyl, —SCH₃ or halogen.

12. A compound of formula I according to claim 11 which is 10-(3-cyclopropyl-1,2,4-oxadiazol-5-yl)-3-methoxy-9H-imidazo[1,5-a][1,2,4]triazolo[4,3-d][1,4]benzodiazepine, 10-(3-cyclopropyl-1,2,4-oxadiazol-5-yl)-3-methyl-9H-imidazo[1,5-a][1,2,4]triazolo[4,3-d][1,4]benzodiazepine, 10-(3-cyclopropyl-1,2,4-oxadiazol-5-yl)-3-bromo-9H-imidazo[1,5-a][1,2,4]triazolo[4,3-d][1,4]benzodiazepine or 10-(3-cyclopropyl-1,2,4-oxadiazol-5-yl)-3-methylsulfanyl-9H-imidazo[1,5-a][1,2,4]triazolo[4,3-d][1,4]benzodiazepine.

13. A compound of formula I according to claim 10, wherein R³ is —CH₂-indolyl or —CH₂-phenyl, optionally substituted by —N(CH₃)₂ and R¹ is chloro or bromo.

14. A compound of formula I, which is 10-(3-cyclopropyl-1,2,4-oxadiazol-5-yl)-7-(4-dimethylamino-benzyl)-3-bromo-9H-imidazo[1,5-a][1,2,4]triazolo[4,3-d][1,4]benzodiazepine, 3-chloro-10-(5-cyclopropyl-1,2,4-oxadiazol-3-yl)-9H-imidazo[1,5-a][1,2,4]triazolo[4,3-d][1,4]benzodiazepine, 3-chloro-10-(5-cyclopropyl-1,2,4-oxadiazol-3-yl)-7-(1H-indol-3-ylmethyl)-9H-imidazo[1,5-a][1,2,4]triazolo[4,3-d][1,4]benzodiazepine or 7-benzyl-3-chloro-10-(5-cyclopropyl-1,2,4-oxadiazol-3-yl)-9H-imidazo[1,5-a][1,2,4]triazolo[4,3-d][1,4]benzodiazepine.

15. A process for preparing a compound of formula I as described in claim 1, comprising:

a) reacting a compound of formula

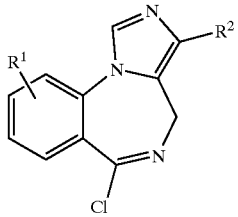

II with a compound of formula

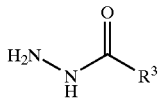

III forming a compound of formula

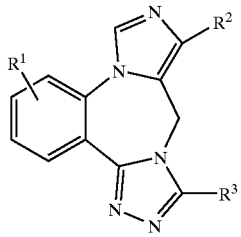

I wherein the substituents $R^1$–$R^3$ have the significances given in claim 1.

16. A process for preparing a compound of formula I as described in claim 1, comprising:

a) reacting a compound of formula

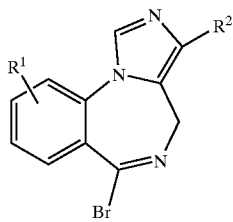

IV with

forming a compound of formula

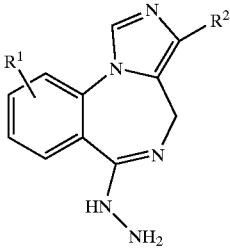

V this compound with $R^3$—$C(OC_2H_5)_3$    VI forming a compound of formula

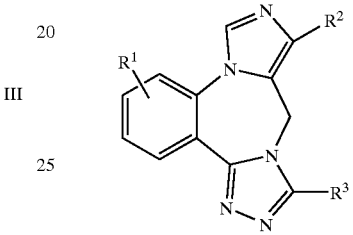

wherein $R^1$–$R^3$ have the significances given in claim 1.

17. A method of treating Alzheimer's disease in a patient comprises administering an effective amount of a compound of formula I,

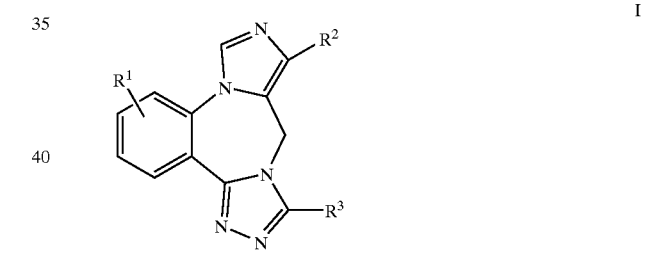

I wherein $R^1$ is hydrogen, halogen, lower alkyl, lower alkoxy, hydroxy, cyano, trifluoromethyl, trifluoromethoxy or lower alkylthio;

$R^2$ is —C(O)O-lower alkyl, unsubstituted isoxazolyl, 1,2,4-oxadiazol-3-yl or 1,2,4-oxadiazol-5-yl, or isoxazolyl, 1,2,4-oxadiazol-3-yl or 1,2,4-oxadiazol-5-yl substituted by lower alkyl, trifluoromethyl or cycloalkyl;

$R^3$ is hydrogen, lower alkyl, —$(CH_2)_n$-cycloalkyl, —$(CH_2)_n$-halogen, —$(CH_2)_n$-pyridin-4-yl, or unsubstituted —$(CH_2)_n$-phenyl, or —$(CH_2)_n$-phenyl substituted by one or two substituents selected from the group consisting of lower alkoxy, halogen, —$SO_2CH_3$, phenyl, $OCF_3$, nitro, $CF_3$, —$NR_2$, or is unsubstituted —$(CH_2)_n$-indolyl, or —$(CH_2)_n$-indolyl substituted by lower alkyl or lower alkoxy, or is pyrrolidinyl-5-oxo, —C(O)—$NR_2$, —$(CH_2)_n$-OH, —$(CH_2)_n$-$NR_2$ or —$(CH_2)_n$-benzo[1,3]dioxole;

R is hydrogen or lower alkyl; and n is 0, 1, 2 or 3; or a pharmaceutically acceptable salt thereof.

18. The method of treating Alzheimer's disease of claim 17 wherein the administering step further comprises selecting and administering a compound of formula I from the group consisting of ethyl 3-methoxy-9H-imidazo[1,5-a][1,2,4]triazolo[4,3-d][1,4]-benzodiazepine-10-carboxylate, ethyl 3-methyl-9H-imidazo[1,5-a][1,2,4]triazolo[3,4-d][1,4]benzodiazepine-10-carboxylate, ethyl 3-bromo-9H-imidazo[1,5-a][1,2,4]triazolo[4,3-d][1,4]-benzodiazepine-10-carboxylate, 10-(3-cyclopropyl-1,2,4-oxadiazol-5-yl)-3-methoxy-9H-imidazo[1,5-a][1,2,4]triazolo[4,3-d][1,4]benzodiazepine, 10-(3-cyclopropyl-1,2,4-oxadiazol-5-yl)-3-methyl-9H-imidazo[1,5-a][1,2,4]triazolo[4,3-d][1,4]benzodiazepine, 10-(3-cyclopropyl-1,2,4-oxadiazol-5-yl)-3-bromo-9H-imidazo[1,5-a][1,2,4]triazolo[4,3-d][1,4]benzodiazepine, 10-(3-cyclopropyl-1,2,4-oxadiazol-5-yl)-3-methylsulfanyl-9H-imidazo[1,5-a][1,2,4]triazolo[4,3-d][1,4]benzodiazepine, ethyl 9H-imidazo[1,5-a][1,2,4]triazolo[3,4-d][1,4]benzodiazepine-10-carboxylate;

10-(3-cyclopropyl-1,2,4-oxadiazol-5-yl)-9H-imidazo[1,5-a][1,2,4]triazolo[4,3-d][1,4]benzodiazepine, ethyl 3-fluoro-9H-imidazo[1,5-a][1,2,4]triazolo[4,3-d][1,4]benzodiazepine-10-carboxylate, 10-(3-cyclopropyl-1,2,4-oxadiazol-5-yl)-3-fluoro-9H-imidazo[1,5-a][1,2,4]triazolo[4,3-d][1,4]benzodiazepine, ethyl 3-chloro-9H-imidazo[1,5-a][1,2,4]triazolo[4,3-d][1,4]benzodiazepine-10-carboxylate, 3-chloro-10-(3-cyclopropyl-1,2,4-oxadiazol-5-yl)-9H-imidazo[1,5-a][1,2,4]triazolo[4,3-d][1,4]benzodiazepine, ethyl 3-methoxy-7-methyl-9H-imidazo[1,5-a][1,2,4]triazolo[4,3-d][1,4]-benzodiazepine-10-carboxylate, ethyl 3-methoxy-7-(1H-indol-3-ylmethyl)-9H-imidazo[1,5-a][1,2,4]triazolo[4,3-d][1,4]-benzodiazepine-10-carboxylate, ethyl 7-hydroxymethyl-3-methoxy-9H-imidazo[1,5-a][1,2,4]triazolo[4,3-d][1,4]-benzodiazepine-10-carboxylate, ethyl 3-methoxy-7-(3-methoxybenzyl)-9H-imidazo[1,5-a][1,2,4]triazolo[4,3-d][1,4]-benzodiazepine-10-carboxylate, ethyl 3-methoxy-7-[(7-methoxy-1H-indol-3-yl)methyl]-9H-imidazo[1,5-a][1,2,4]triazolo[4,3-d][1,4]-benzodiazepine-10-carboxylate, ethyl 3-bromo-7-[(1H-indol-3-yl)methyl]-9H-imidazo[1,5-a][1,2,4]triazolo[4,3-d][1,4]-benzodiazepine-10-carboxylate, and ethyl 3-bromo-7-(3-methoxy-benzyl)-9H-imidazo[1,5-a][1,2,4]triazolo[4,3-d][1,4]-benzodiazepine-10-carboxylate to a patient in need of such treatment.

* * * * *